United States Patent [19]

Hogan et al.

[11] Patent Number: 5,653,759
[45] Date of Patent: Aug. 5, 1997

[54] IN-VIVO METHOD FOR REPAIRING A RUPTURED SEGMENT OF A THERAPEUTIC APPLIANCE SURGICALLY POSITIONED PREVIOUSLY WITHIN THE BODY OF A LIVING HUMAN

[75] Inventors: John D. Hogan, Gloucester; Ducksoo Kim, Dover, both of Mass.

[73] Assignee: Beth Israel Hospital Assoc. Inc., Boston, Mass.

[21] Appl. No.: 503,482

[22] Filed: Jul. 18, 1995

[51] Int. Cl.⁶ .............................. A61F 2/02; A61B 17/56
[52] U.S. Cl. .............................. 623/11; 128/898; 606/78; 607/116
[58] Field of Search .................... 607/116, 122; 128/898; 623/1, 2, 3, 11, 16, 18, 20, 22, 24; 606/108, 78

[56] References Cited

U.S. PATENT DOCUMENTS 5,474,557  12/1995  Mai ............................................ 606/78

*Primary Examiner*—David H. Willse
*Assistant Examiner*—Francis K. Cuddihy
*Attorney, Agent, or Firm*—David Prashker

[57] ABSTRACT

The present invention is an in-vivo methodology for repairing a ruptured or fragmented segment of a pre-existing therapeutic appliance which has been previously surgically positioned or implanted within the body of a living human. The repair methodology provides for specific apparatus and techniques using a guiding catheter and deformable, thermoelastic shape-memory alloy rods in order to access and repair the flawed or failing therapeutic appliance in place. The repair methodology thus eliminates the need for surgical excision procedures and avoids the requirement for replacement substitute units in order to alleviate and solve the problem of having a flawed therapeutic appliance in-vivo.

15 Claims, 18 Drawing Sheets

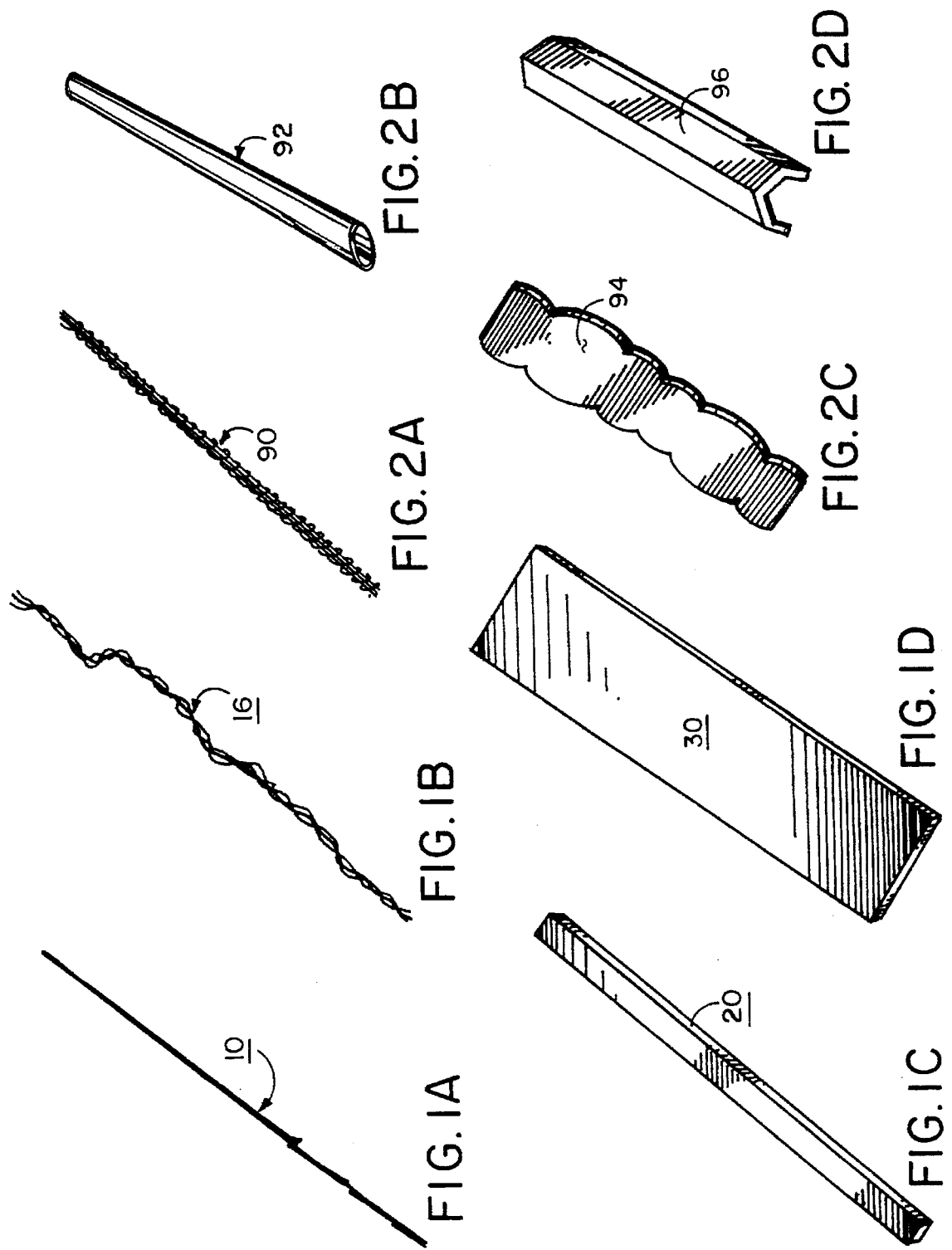

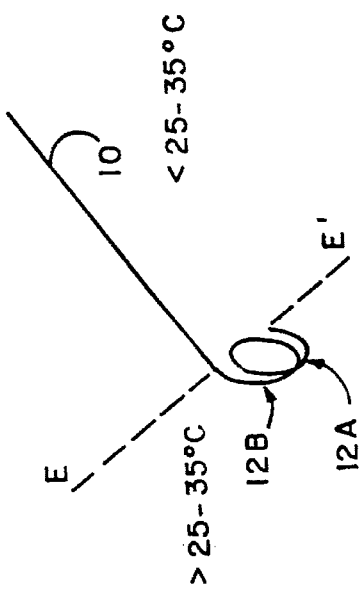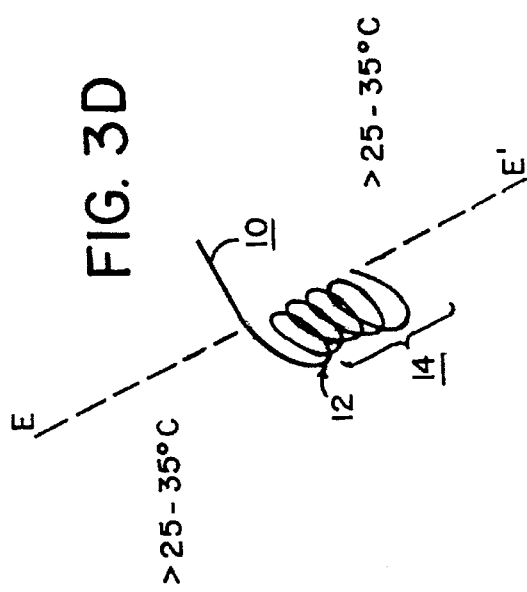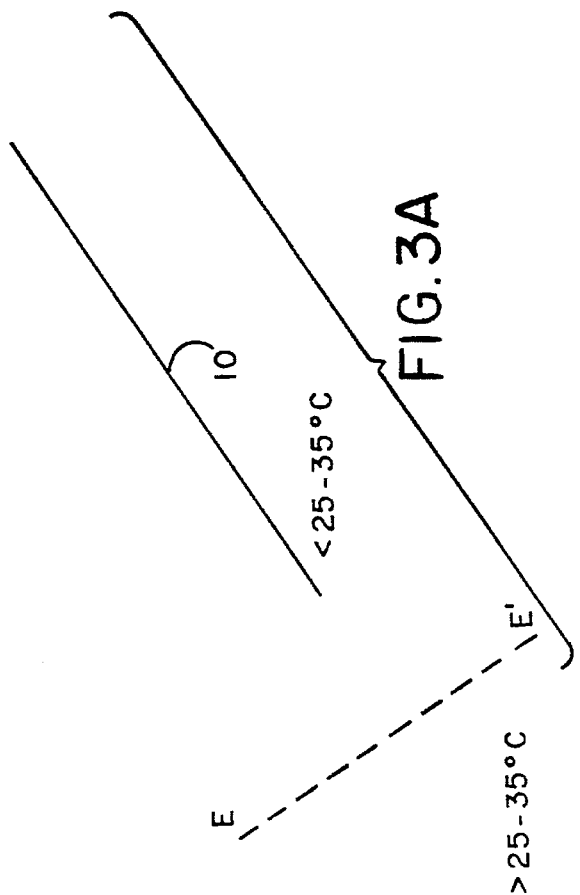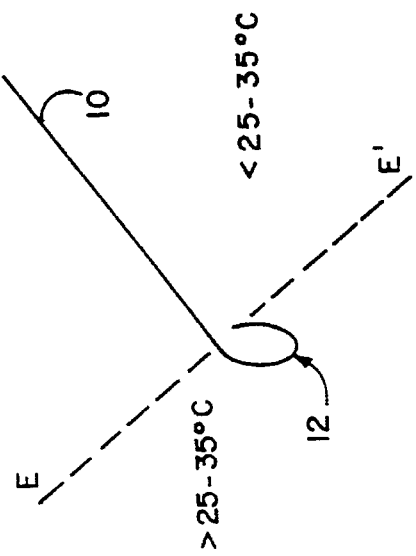

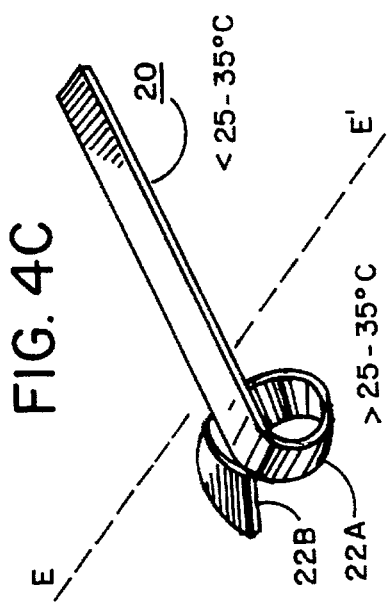
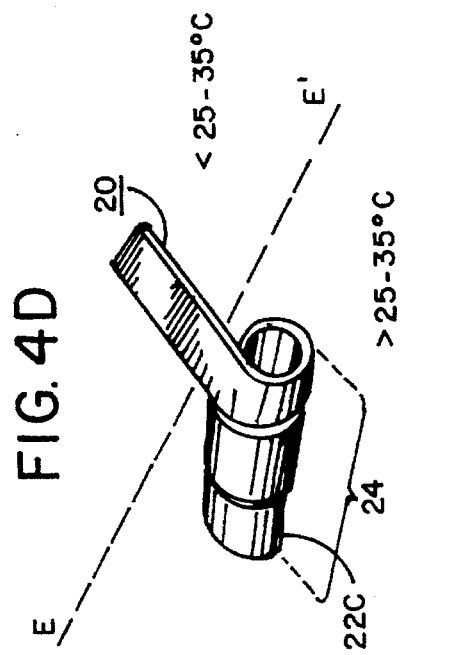
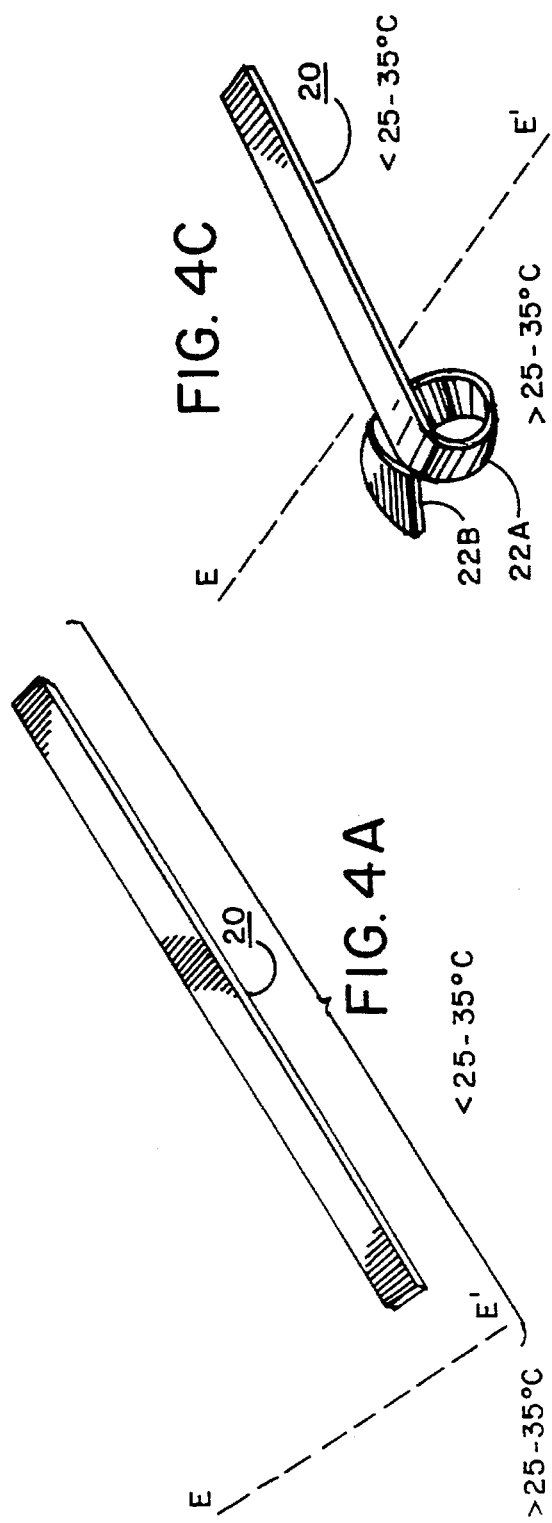
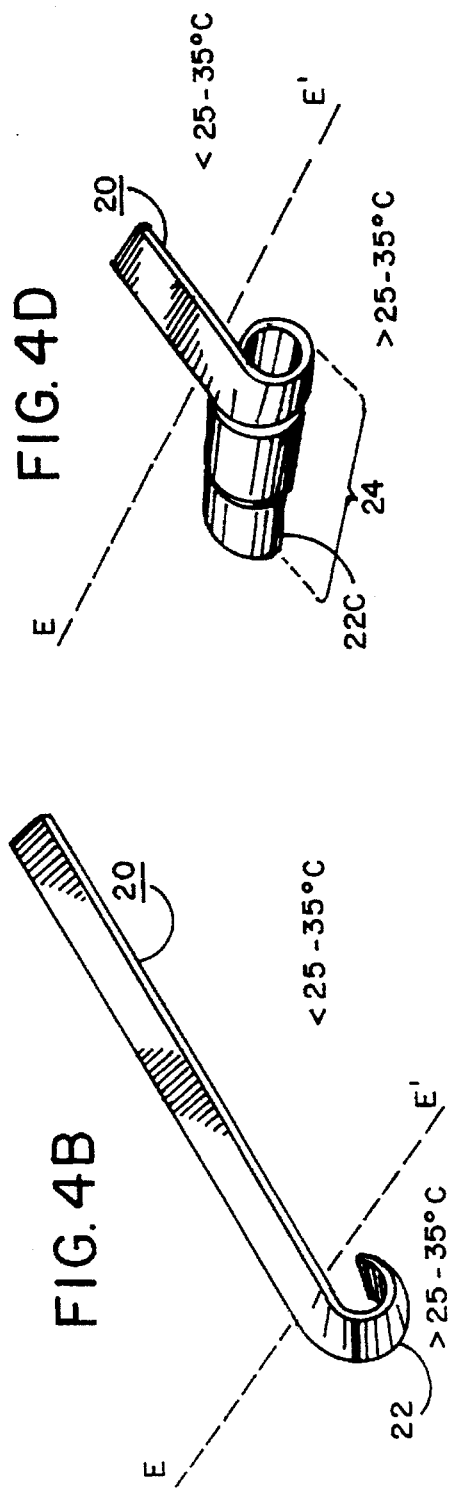

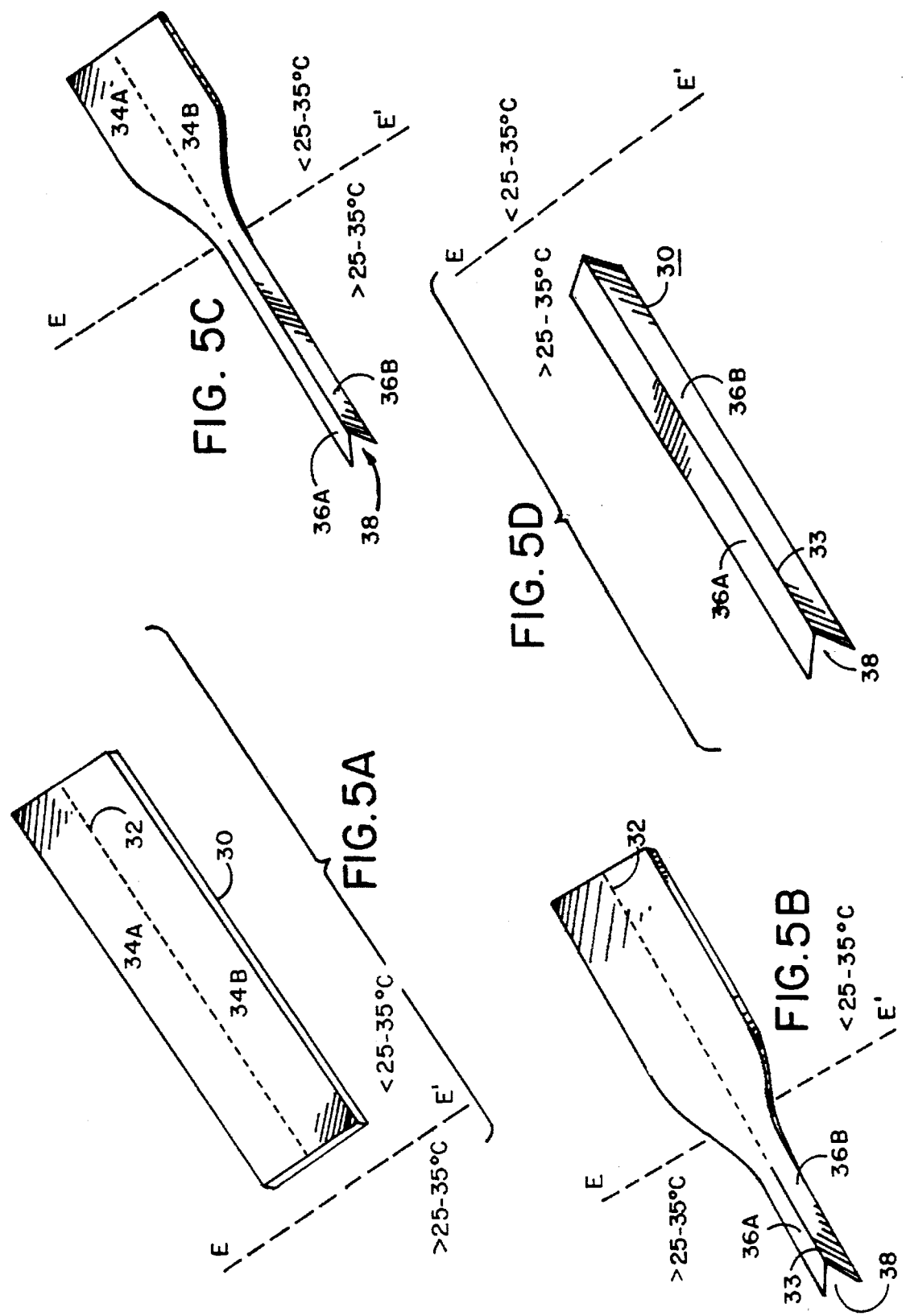

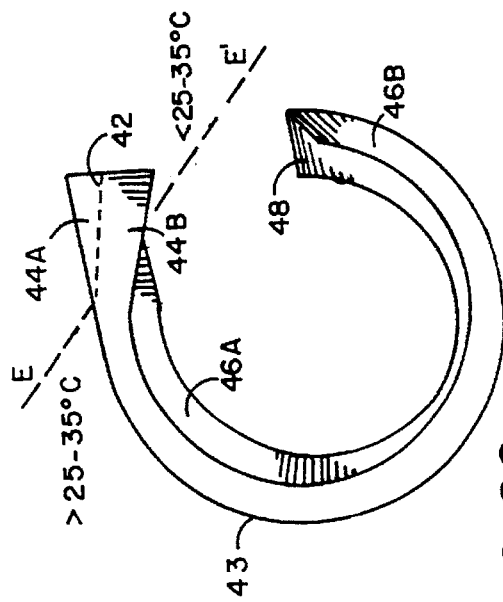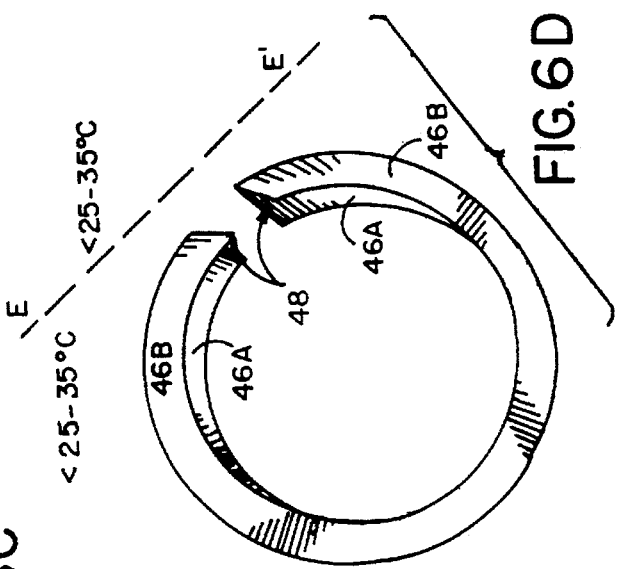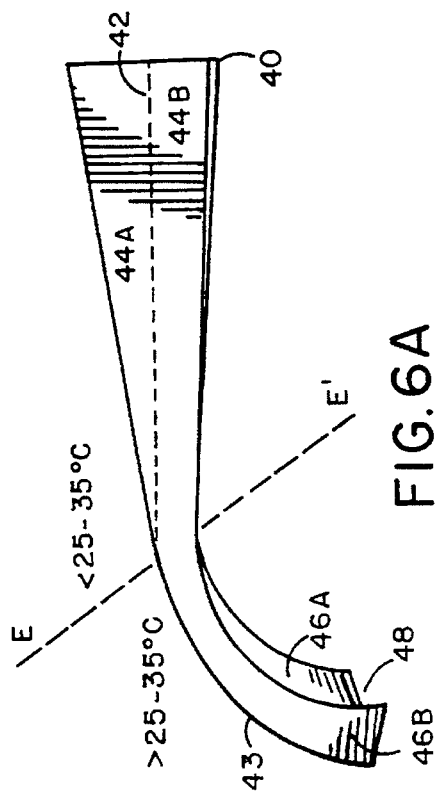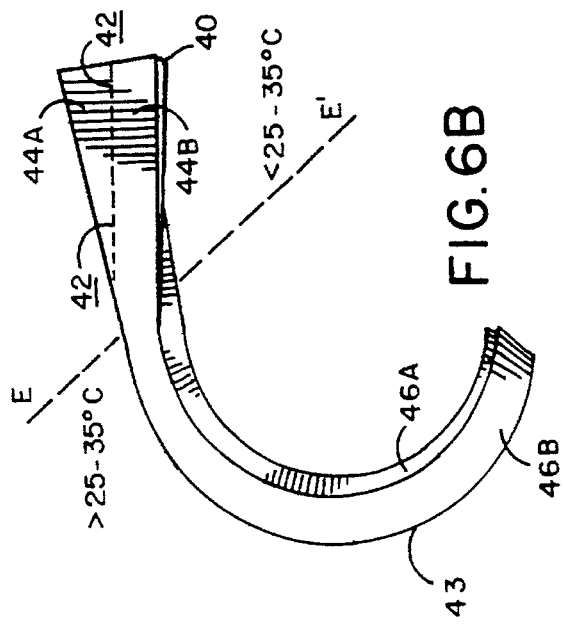

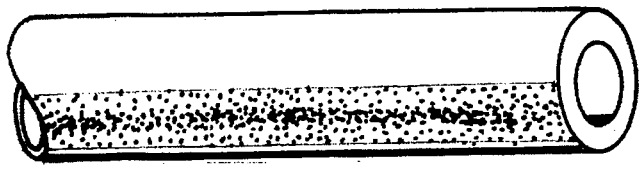 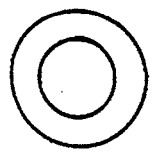
FIG. 9A  FIG. 9B
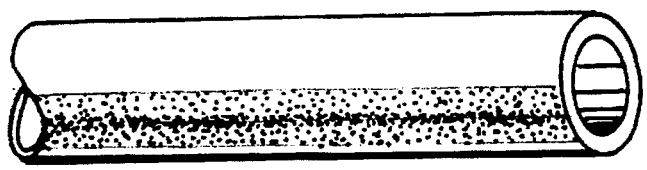 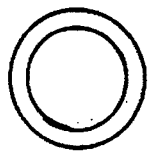
FIG. 10A  FIG. 10B
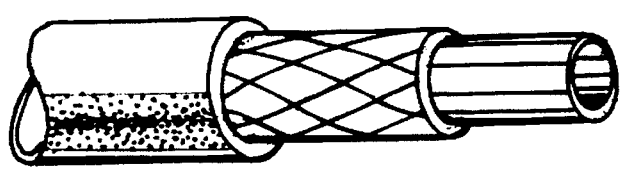 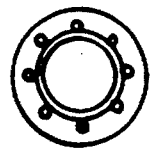
FIG. 11A  FIG. 11B
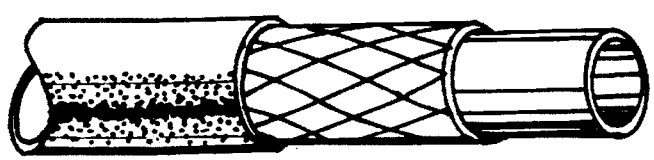 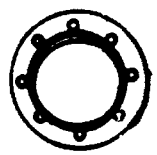
FIG. 12A  FIG. 12B

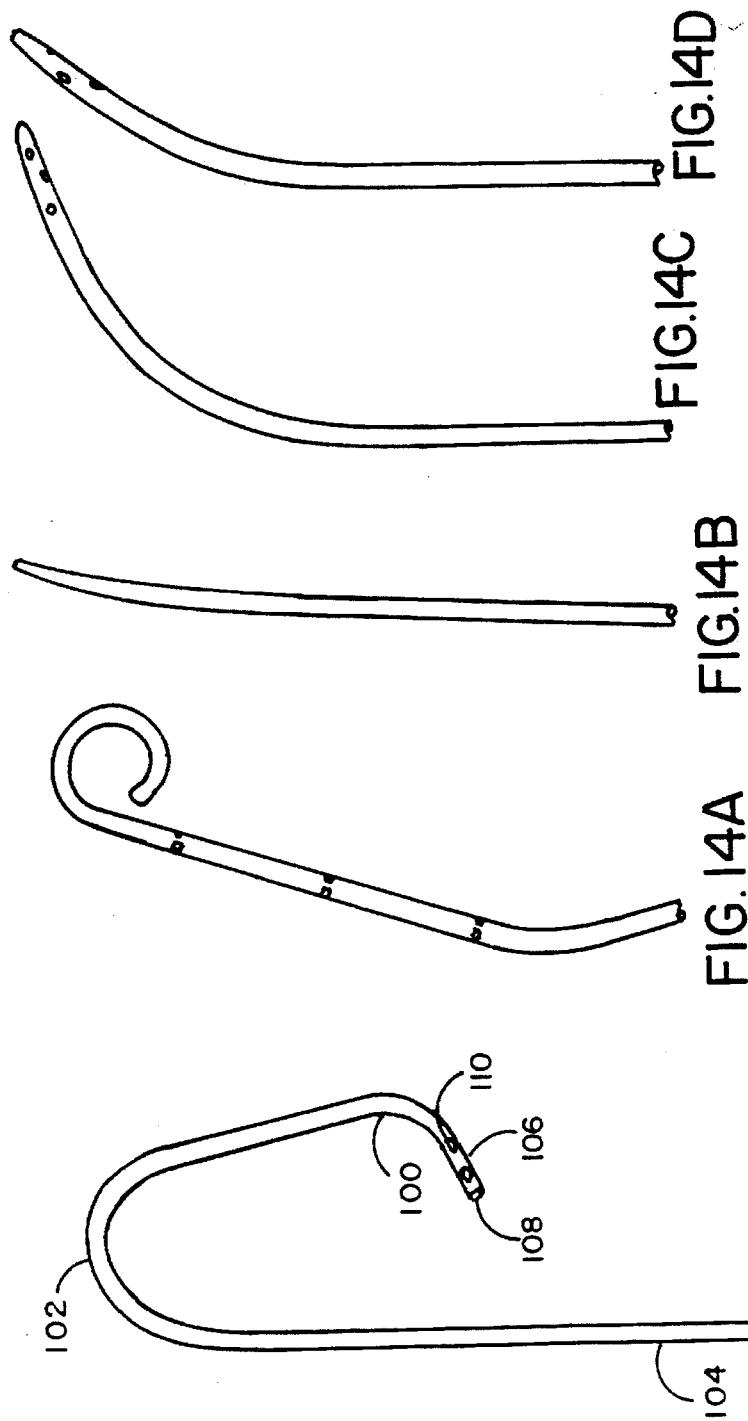

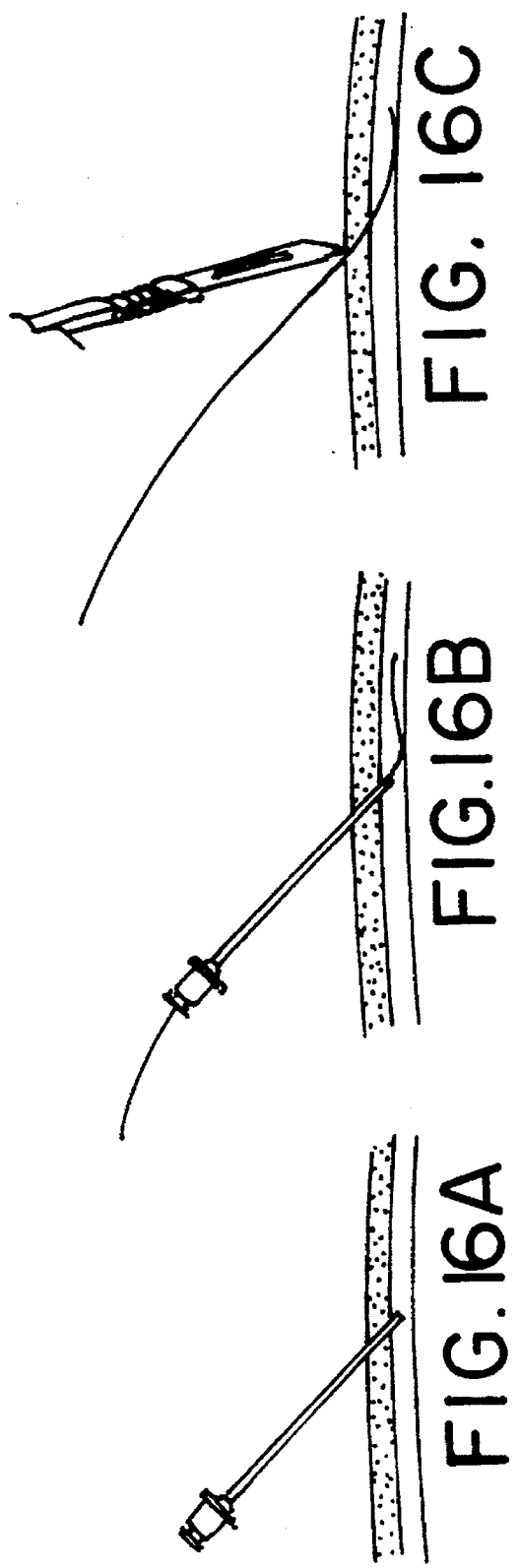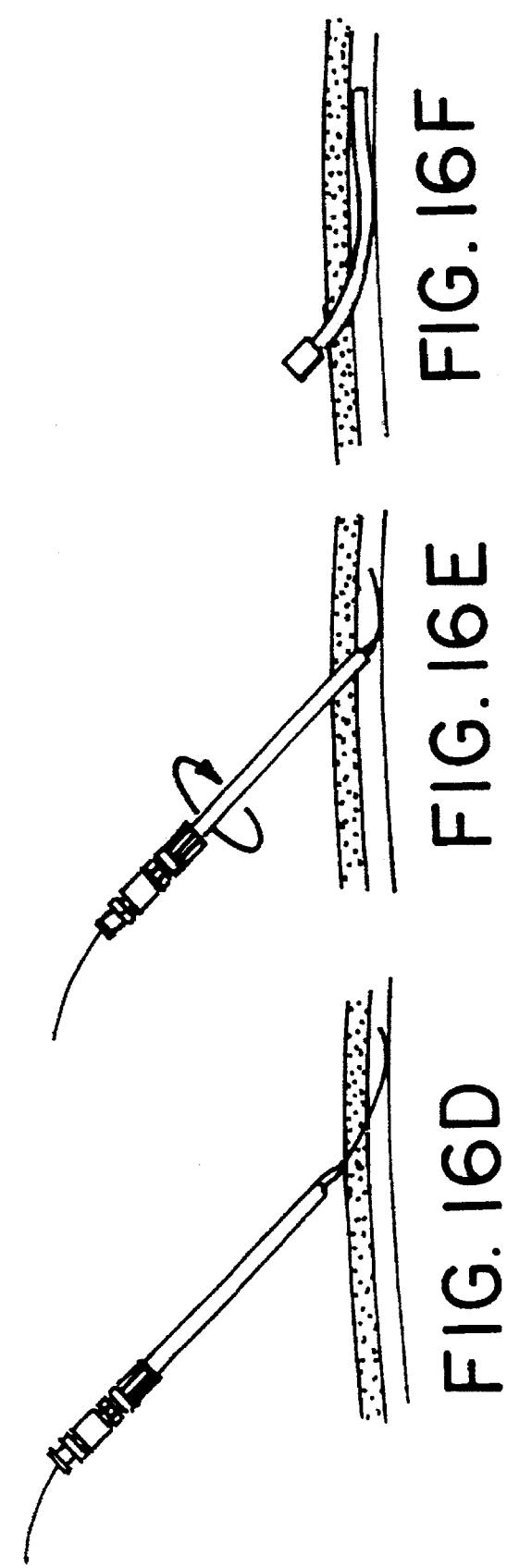

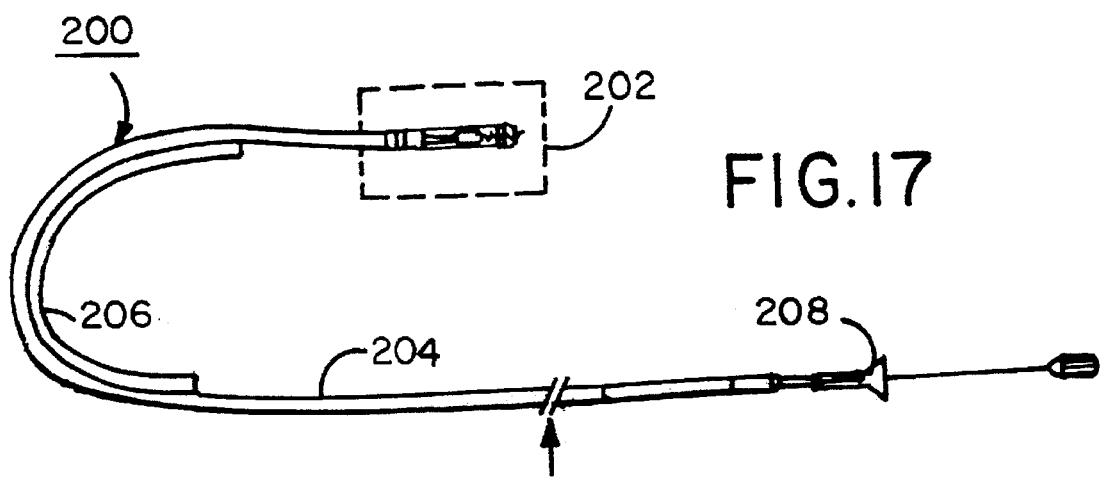
FIG. 17
FIG. 18
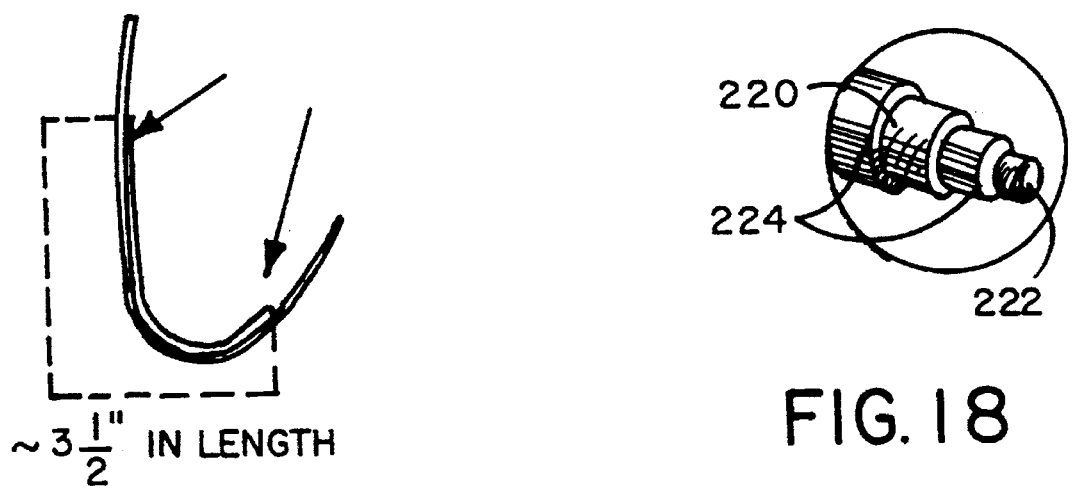
~ 3½" IN LENGTH
FIG. 19
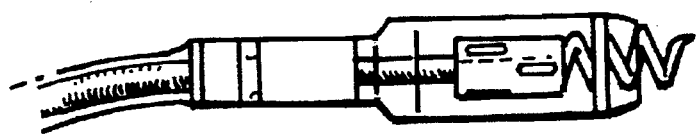
FIG. 20

FIG.22A FIG.22B
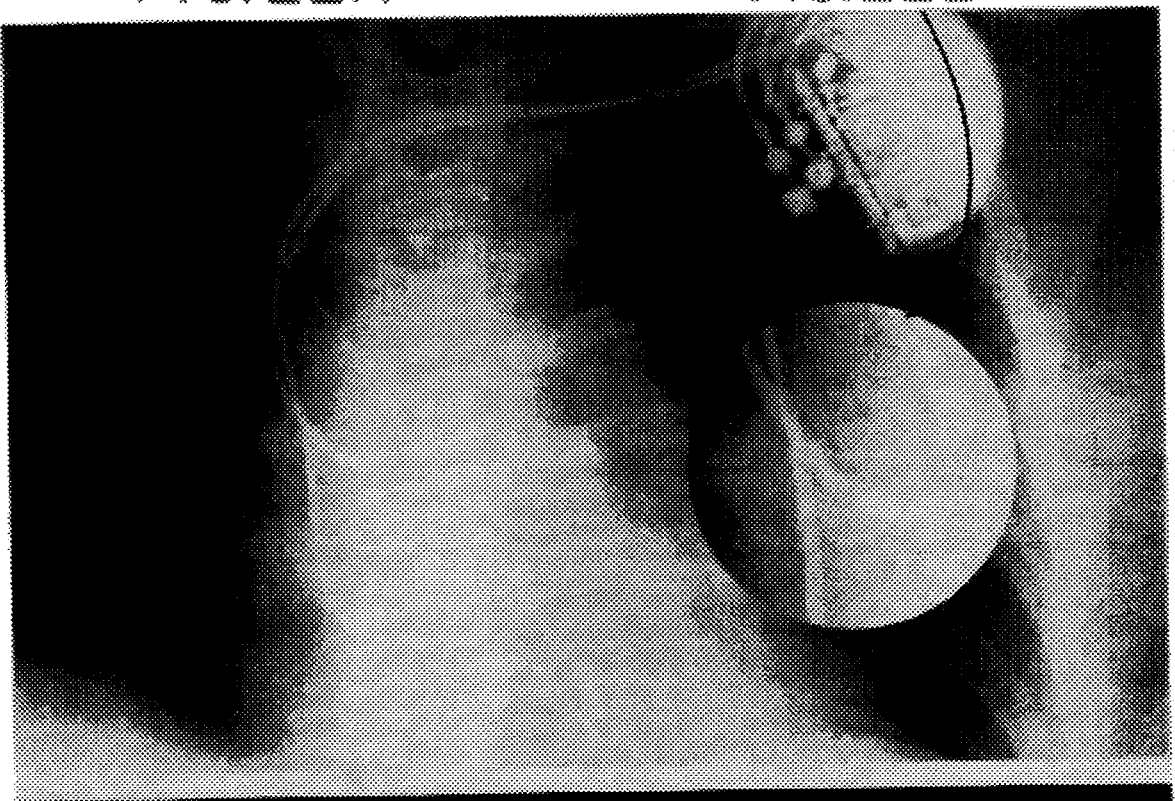
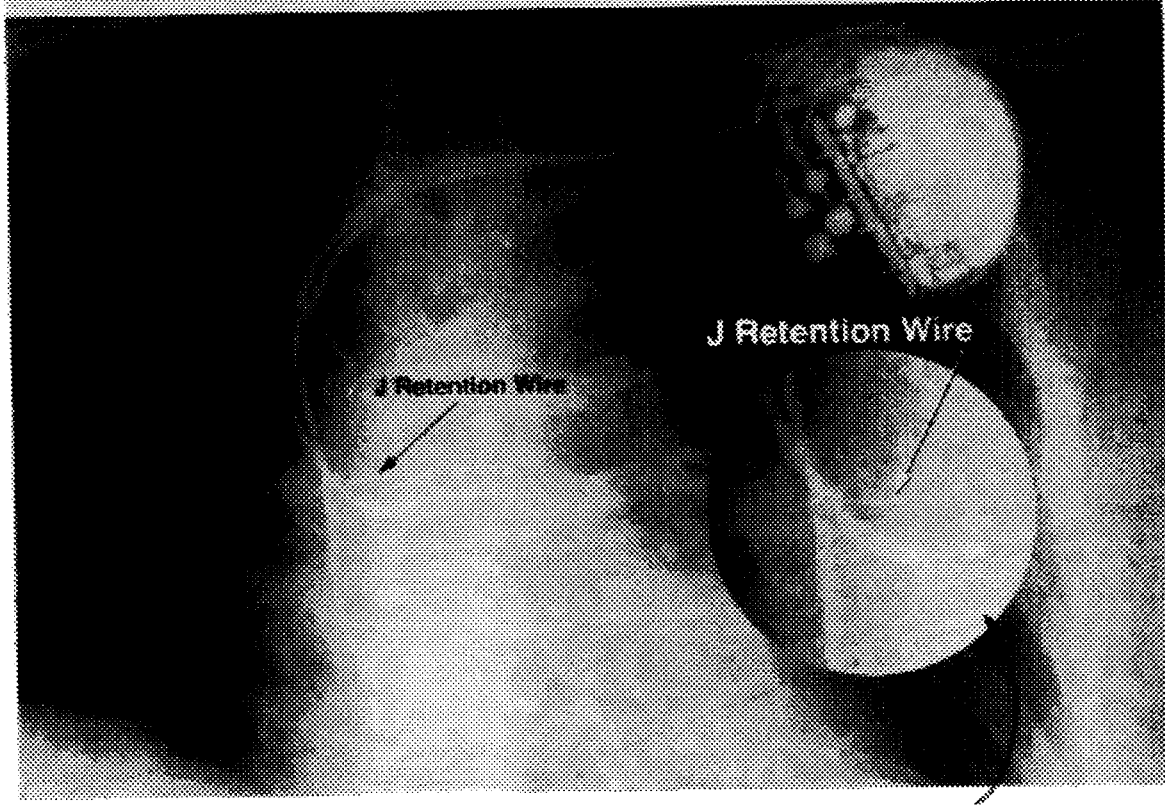
FIG.23A FIG.23B

FIG.26A
FIG.27A
FIG.26B
FIG.27B

IN-VIVO METHOD FOR REPAIRING A RUPTURED SEGMENT OF A THERAPEUTIC APPLIANCE SURGICALLY POSITIONED PREVIOUSLY WITHIN THE BODY OF A LIVING HUMAN

FIELD OF THE INVENTION

The present invention is concerned generally with the frequently occurring problem of falling therapeutic appliances which have become broken, have fractured, or become ruptured after being surgically implanted or positioned within the body of a living subject; and is specifically directed to in-vivo methods for repairing a ruptured segment of a surgically positioned therapeutic appliance without need for surgically excising the flawed appliance and surgically replacing it with a substitute device.

BACKGROUND OF THE INVENTION

For over a century to date, physicians and surgeons have created and clinically utilized an ever increasing range and diversity of artificially-created therapeutic appliances as an effective means of repair and treatment for patients. When considered in historical perspective, such therapeutic appliances have been primarily developed and most intensively used by medical practitioners in orthopedics, radiology, surgery, and cardiology; and typically may be broadly divided into two separate and distinct general categories of prostheses (or prosthetic devices) and physiological-assist articles or apparatus. It will be recognized and appreciated, however, that due to the disparity of approach and medical assessment as well as the specific medical needs of an individual human patient, the different medical areas of orthopedics, radiology, surgery, and cardiology have generated a variety of diverse constructions, structures, and innovations in therapeutic appliances which meet the singular requirements of that medical specialty.

For example, orthopedics, being concerned with a correction of skeletal deformities, have concentrated heavily if not exclusively on the creation of prostheses which serve as a complete substitute and artificial replacement for a missing part of the human skeleton. Thus, orthopedic prostheses include structural devices such as a plate in the skull; a graft replacement for a bone; a synthetic patella (or kneecap); and a surgical nail or spike by which to anchor a ligament, or tendor, a bone to a bone. Similarly, other prosthetic devices include mechanical joint or flow connectors such as a hip or shoulder joint replacement, and a prosthetic hearing aid.

In comparison, the therapeutic appliances generated and developed by the departments of radiology and cardiology have been frequently physiological-assist articles rather than prosthetic devices as such. As used herein, a physiological-assist article or apparatus does not serve as a substitute or replacement part for a missing or destroyed organ, structure, or tissue in the living body. Rather, a physiological-assist article is an auxiliary construction and structure which is surgically positioned or implanted into the living body of the patient in order to maintain, control, or additionally regulate the existing organs and tissues of the body; and serves as an aid in the performance of their intended function during life. Physiological-assist articles are thus supplemental, often incremental, and frequently duplicative therapeutic constructions and structures which aid, abet, and help to supply what is needed in a secondary, adjunct, or subordinate role to accomplish a medical result, objective, or end. Thus, physiological-assist articles are not themselves prostheses in that they do not and cannot serve as a complete substitute for or replacement of a missing or destroyed organ, tissue, or body structure.

Some of the most commonly known and utilized physiological-assist articles are cardiovascular or gastrointestinal devices; and these generally may be segregated and distinguished into not less than four distinct groups, which are: (a) structural assist devices which are exemplified by stents used for treating obstructive or abnormally dilated lesions (aneurysms) involving blood vessels, bile ducts, ureters and the gastrointestinal tract; (b) mechanical flow assist articles such as blood filter devices positioned in the major blood vessels for collecting clots; (c) electrical assist articles such as cardiac pacemakers positioned in the ventricle or atrium or both of the heart; and finally, (d) electromechanical articles such as cardiac assist devices including temporary or permanent artificial heart chambers, ventricular assist pumps and drives, and artificial heart stimulators. All of these may be properly considered as physiological-assist articles rather than prostheses.

In addition, there are a number of proper or true prosthetic devices originating from the radiology and cardiology departments. Representative of these today are synthetic blood vessels intended as complete substitutes and/or replacements for specific sections of arteries or veins. Similarly, the ongoing development and use of an artificial heart as a partial or complete substitute and replacement for a defective native heart is today a rapidly developing and ongoing area of major research for prostheses. It will be recognized and appreciated that these specific instances and examples are; merely illustrative and representative of the range and diversity of articles and devices commonly known and used as therapeutic appliances for the human patient today.

Given the range, variety, and diversity of therapeutic appliances available as well as in frequent usage today as surgically implanted or positioned articles and devices within the human body, the greatest danger and fear of the patient is that the implanted therapeutic appliance might break, fracture, or rupture at an indefinite time in the future. Thus, if the electrical lead of a cardiac pacemaker previously imbedded into the heart wall fractures or ruptures; or if a flange of a heart valve cracks; or if an intravascular stent in a blood vessel begins to fragment; or if the prosthesis of the bone becomes partially or completely detached, there is typically only one recourse left to both the physician/ surgeon and the afflicted human patient—a complete surgical excision of the defective structure and a replacement with a new, substitute device.

To be sure, this course of remedial surgery is not undertaken lightly or casually; and the risk to the patient from a complete surgical excision operation with a subsequent complete replacement of the defective device can be a very hazardous and extremely dangerous procedure. The reasons for this high risk and extreme danger are twofold: First, the surgical excision procedure actually destroys a portion of the existing normal tissue surrounding the flawed appliance as a consequence of surgically excising the flawed device from the position in which it has been implanted previously. Such surgical excision almost always causes some nerve and/or vascular tissue loss as well as some structural bone and/or muscle loss in the local area surrounding the therapeutic appliance within the body. Thus, surgical removal of the flawed appliance surgically must cause some tissue destruction and some permanent loss of function or support even when the new substitute appliance is implanted. Second, it is most common for those who are of poor medical condition, or are of advancing age, or are physically frail to be persons which typically require the in-vivo positioning or implantation of a therapeutic appliance in the first instance. Thus, it is typically persons with poor or troublesome heart conditions which require the placement of cardiac pacemakers; and it is usually those persons afflicted with an aneurysm which require stent as a therapeutic appliance; and it is commonly the person who has suffered a fracture of bone who requires a bone prosthesis to replace the now destroyed original bone. Thus, all of these persons are medically disadvantaged in the original circumstances which required the surgical positioning of a therapeutic appliance in order that their medical condition be improved and their health enhanced. Such people incur a very high risk and hazard from such surgical excision procedures and the inherent dangers of such intensive surgery using generalized anesthesia for a prolonged time. For the extremely frail, the very aged, and the medically unfit, the choice sometimes reduces itself to a single question: Is it to be a death by waiting for the flawed therapeutic appliance to fail completely such that the natural life function can no longer be sustained; or a death on the surgical operating table at a chosen time and place due to the inability of the patient to tolerate the surgical excision and appliance replacement procedure!

It will be recognized and appreciated, therefore, that there has been a long standing and continuing need for a meaningful alternative to surgical excision and therapeutic appliance replacement as the sole remedy available to date. While some patients are properly fit candidates for the surgical excision and replacement procedure, a great proportion of humans having therapeutic appliances implanted within their bodies cannot risk the hazards of such radial surgery. For such persons, their choices are few or none. Accordingly, were an in-vivo method for repairing a ruptured segment of a therapeutic appliance already surgically positioned within the body of a living human to become available, such an in-vivo repair method would be an outstanding achievement, be an immeasurable benefit, and be a meaningful alternative to the predicted dire consequences of submitting to a surgical excision and replacement procedure.

SUMMARY OF THE INVENTION

The present invention is an in-vivo method for repairing a ruptured segment of a therapeutic appliance which has been previously surgically positioned within the body of a living human, said in-vivo repair method comprising the steps of:

providing at least one metal alloy rod of predetermined dimensions and comprised of a deformable thermoelastic shape-memory alloy, at least a portion of said elongated thermoelastic metal rod being substantially in a first deformed-shape configuration at temperatures less than about 25°–35° C. while transforming into a memory-shaped second configuration at temperatures greater than about 25°–35° C.;

providing a controlling flexible catheter having at least one tubular wall of set axial length, at least one proximal end for entry, at least one distal end for egress, and at least one internal lumen of a volume sufficient to allow for on-demand controlled passage therethrough of said elongated thermoelastic metal rod;

surgically introducing a portion of the axial length of said controlling flexible catheter into the body of the living human such that said distal end of said surgically introduced catheter becomes positioned adjacent to the ruptured segment of the therapeutic appliance in-vivo;

maintaining at least a portion of said internal lumen of said surgically introduced catheter at a temperature less than about 25°–35° C.;

placing said thermoelastic metal alloy rod in said first deformed-shape configuration through said proximal end into said internal lumen of said surgically introduced catheter such that an on-demand controlled extension and retraction of said metal alloy rod through said internal lumen of said catheter is achieved; controllably extending a portion of said thermoelastic metal alloy rod on-demand through said internal lumen to exit via said distal end of said surgically introduced and adjacent positioned catheter into the in-vivo temperature environment of the living body such that said exiting portion of said thermoelastic metal alloy transforms into said memory-shaped second configuration; and extending the remainder of said thermoelastic metal alloy rod on-demand through said internal lumen to exit via said distal end of said surgically introduced and adjacently positioned catheter into the in-vivo temperature environment of the living body such that said exiting memory-shaped second configuration of said metal alloy at least partially overlays the ruptured segment of the therapeutic appliance as an in-vivo repair.

BRIEF DESCRIPTION OF THE FIGURES

The present invention may be more easily and completely understood when taken in conjunction with the accompanying drawings, in which:

FIGS. 1A–1D are illustrations of some preferred embodiments for the elongated metal rod formed of deformable, thermoelastic shape-memory alloy;

FIGS. 2A–2D are illustrations of some other embodiments for the elongated metal rod formed of deformable, thermoelastic shape-memory alloy;

FIGS. 3A–3D are sequential illustrations showing the transformation in configuration of a first preferred embodiment of the elongated metal rod when passing from a temperature zone less than 30°–35° C. into another temperature zone greater than 30°–35° C.;

FIGS. 4A–4D are sequential illustrations showing the transformation in configuration of a second preferred embodiment of the elongated metal rod when passing from a temperature zone less than 30°–35° C. into another temperature zone greater than 30°–35° C.;

FIGS. 5A–5D are sequential illustrations showing the transformation in configuration of a third preferred embodiment of the elongated metal rod when passing from a temperature zone less than 30°–35° C. into another temperature zone greater than 30°–35° C.;

FIGS. 6A–6D are sequential illustrations showing the transformation in configuration of a fourth preferred embodiment of the elongated metal rod when passing from a temperature zone less than 30°–35° C. into another temperature zone greater than 30°–35° C.;

FIGS. 9A and 9B are perspective and cross-sectional views of a single wall catheter tube of normal thickness;

FIGS. 10A and 10B are perspective and cross-sectional views of a single wall catheter tube of reduced thickness;

FIGS. 11A and 11B are perspective and cross-sectional views of a multiple-wall catheter body of normal thickness;

FIGS. 12A and 12B are perspective and cross-sectional views of a multiple-wall catheter tube of reduced thickness;

FIG. 13 is an illustration of the distal end of a conventional guiding catheter;

FIGS. 14A–14D are illustrations showing alternative constructions for the distal ends of a guiding catheter;

FIGS. 16A through 16F are sequential illustrations showing a preferred technique for introducing the guiding catheter into a blood vessel in the body of a living patient;

FIG. 17 is an illustration of the J-retention wire and the pacing electrical lead commonly used with a cardiac pacemaker;

FIG. 18 is a cut-away perspective illustration of the electrical pacing lead of FIG. 17;

FIG. 19 is a detailed view of the J-retention wire forming a part of the pacing lead of FIG. 17;

FIG. 20 is a detailed view of the screw-thread distal end of the electrical pacing lead of FIG. 17;

FIGS. 22A and 22B are fluorophotographs (radiographs) showing the wide-field and detailed views of the imbedded pacing lead and fragmented J-retention wire in a cardiac pacemaker unit existing in-vivo within a living human;

FIGS. 23A and 23B are marked illustrations of FIGS. 22A and 22B respectively;

FIGS. 26A and 26B are fluorophotographs showing another kind of fragmented J-retention wire in a pacing lead existing in-vivo within another living human;

FIGS. 27A and 27B are fluorophotographs showing a third instance of a ruptured J-retention wire in a pacing lead existing in-vivo within a third living person;

DETAILED DESCRIPTION OF THE PRESENT INVENTION

Figure 7:
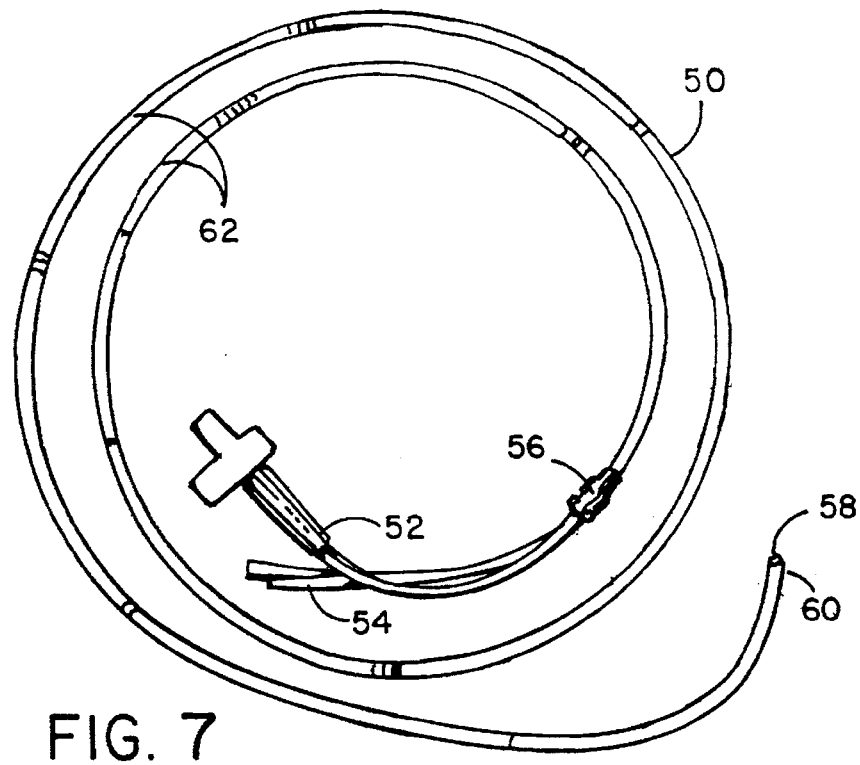
FIG. 7 is an overhead view illustration of a conventional known guiding catheter.

The present invention is an in-vivo method for repairing a therapeutic appliance: which has been previously positioned, implanted, or inserted within the body of a living human. Foremost therefore, it is essential to recognize and appreciate that the present method of repair is not itself either a prosthetic device nor a physiological-assist article-despite the use of specific constructs and apparatus as the means and vehicle, to effect an in-vivo repair of a preexisting therapeutic appliance. It is critical, therefore, to perceive, understand, and realize that the present repair methodology does not offer or present any therapeutic appliance as such; cannot serve as a substitute or replacement for a previously implanted or positioned therapeutic appliance in-vivo; and cannot provide the living human patient with either a functional capability or a structural form equivalent to that provided by a therapeutic appliance of choice.

Instead, the present methodology provides, for the first time insofar as is known to date, an effective methodology and means for repairing an existing prosthetic device or physiological-assist article which has become structurally defective by breaking, fragmenting, or rupturing in one or more sites. The present method for in-vivo repair is thus individually distinct from any particular therapeutic appliance itself; constitutes a separate mending and remedial technique; and utilizes specific materials and means for repair which bear no direct relationship to the flawed therapeutic appliance degenerating or failing in-vivo. Accordingly, it will be noted and acknowledged that there are multiple major benefits and manifold substantial advantages provided by the present methodology, some of which include the following:

1. The present method for in-vivo repair is the sole technique created to date for correcting a rupturing therapeutic appliance as an alternative to complete surgical excision. The present repair technique provides an effective mending of fragmented prosthetic devices and ruptured physiological-assist articles; and may be employed to effect such repairs in-vivo without regard to whether the therapeutic appliance is structural, mechanical, electrical, or electro-mechanical in structure and function.

2. The present method for in-vivo repair is a long-term remedy and is intended as a permanent repair technique which will cure the structural failure of the previously imbedded therapeutic appliance within the body and restore the implanted therapeutic appliance in a mended form to a fully functional capacity and utility. The present invention thus provides a long lasting and stable mend; and offers an in-vivo corrective repair capability for patching up the various breaks, fractures, and cracks such that the mended therapeutic appliance is restored at least into a non-hazardous and partially functional state.

3. The present method for in-vivo repair may be employed in any location, position, or area of the living body so long as a passageway for the introduction of a flexible catheter exists naturally or can be created surgically. Thus, access and a route for catheter conveyance and travel can be effected via a blood vessel (artery or vein); a duct leading into or from a major organ (such as the bile duct); through any tube in the body (such as a bronchial tube); through any major canal or circular passageway in the body (such as the gastro-intestinal canal or any of its component passageways); through an external body cavity (such as the ear canal or vaginal canal); through arty discharge duct (such as a ureter); or any excretory passage (such as the anus and/or rectum). In addition, surgical passageways may be made if and when necessary to access specific areas of the body, such as the thorax, the abdomen, or the cranial cavity. In most if not all instances, a sterile environment and aseptic surgical technique is required and will be observed in accordance with established good medical practices.

4. The present in-vivo repair methodology will in many individual human case instances represent the single and sole alternative for those patients now having an implanted therapeutic appliance which is demonstrably structurally defective. For these living persons, particularly the very aged, the physically unfit, and the medically unstable, the present invention is the only recourse to undergoing the major risk and hazards of surgical removal and replacement of the therapeutic appliance itself. In these particular instances, the present invention is far more than an alternative to the conventional surgical excision procedure; rather, the present invention is the only means for continuing their living existence for an indefinite period of time.

The present method for repairing a cracked, torn, burst, or broken portion of a therapeutic appliance requires and utilizes specifically prepared metal alloy compositions, a flexible guiding catheter, and an introducing and routing technique which positions the distal tip of the guiding catheter adjacent to the flaw or failure in the previously implanted therapeutic appliance. Thus, while the methodology itself is defined as a series of manipulative steps, these requisite manipulations and physical acts employ specific articles and tangible apparatus which must be prepared in advance in order to accomplish the desired goal and objective of repairing the individual defect or fault as it exists in-vivo. For these reasons, a descriptive presentation of the materials and apparatus to be used as tangible entities during the practice of the methodology is provided. In addition, a representative patient problem which exemplifies a most hazardous medical condition caused by a fragmented therapeutic appliance will be disclosed in full, followed by a representative and illustrative showing of how the particular defect in the therapeutic appliance was mended using the present invention.

I. The Deformable, Thermoelastic, Shape-Memory Metal Alloy Compositions

The shape-memory metal alloy compositions to be used with the repair method constitute conventionally known blends and formulated metallic mixtures of nickel and titanium which undergoes a phase transition—that is, a molecular rearrangement of atoms, molecules or ions within a lattice structure—due to a temperature change. The unique capability of shape-memory alloys is that these alloys change shape or configuration as a direct consequence of a change in temperature; and the alloy composition "remembers" its earlier and specifically prepared shape because the phase change affects its structure on the atomic level only, without disturbing the arrangement of the molecules which would otherwise be irreversible.

When these shape-memory alloys are intentionally superheated far above their transition temperature (either electrically or by external heat), a stretched alloy format contracts and exerts considerable force; and the temperature transformed alloy composition will become memory-shaped in a fixed specific configuration. Afterwards, when cooled to below its transition temperature, the alloy composition can then be deformed into other configurations while retaining the fixed "memory" of the particular shape in the earlier superheated condition. Thus, these shape-memory alloy compositions are recognized as being both deformable and thermoelastic, as well as being able to revert to a prepared memory-shaped configuration.

Alloy formulations:

At least twenty different formulations of these alloys are conventionally known to exhibit the shape-memory effect and property, all of these comprising different mixtures of nickel and titanium in varying percentage ratios [*Design News*, Jun. 21, 1993 issue, pages 73–76]. These metal alloys are today utilized in the manufacture of differing products. For example, a range of different shape-memory alloy wires are commercially available in diameters from 0.001–0.010 inches [Dynalloy Inc., Irvine, Calif.]. In addition, surgical anchors having superelastic properties and formed by two or more arcs of wire strands (which can withstand strains exceeding 10%) have been developed [Mitek Surgical Products, Inc., Norwood, Massachusetts]. Also, blood clot filters formed of shaped-memory alloy wires are commercially sold for implantation in large blood vessels such as the vena cava [Nitinol Medical Technologies, Inc., Boston, Mass.]. While these commercially available products illustrate the use of one or more shape-memory alloy formulations by the manufacture of their particular articles, a more general listing of conventionally known properties and characteristics for shape-memory alloy compositions is provided by Table 1 below.

TABLE 1

| Conventionally Known Properties Of Shape-Memory Alloys[1] | |
| --- | --- |
| Transformation Properties | |
| Transformation Temperature | −200 to 110° C. |
| Latent Heat of Transformation | 5.78 cal/g |
| Transformation Strain (for polycrystaline material) | |
| for a single cycle | 8% maximum |
| for $10^2$ cycles | 6% |
| for $10^5$ cycles | 4% |
| Hysteresis* | 30 to 50° C. |
| Physical Properties | |
| Melting point | 1300° C. (2370° F.) |
| Density | 6.45 g/cm$^3$ (0.233 lb/in$^3$) |
| Thermal Conductivity | |
| austenite | 0.18 W/cm · °C. (10.4 BTU/ft · hr · °F.) |
| martensite | 0.086 W/cm · °C. (5.0 BTU/ft · hr · °F.) |
| Coefficient of Thermal Expansion | |
| austenite | $11.0 \times 10^{-6}$/°C. ($6.11 \times 10^{-6}$/°F.) |

TABLE 1-continued

Conventionally Known Properties Of
Shape-Memory Alloys[1]

| | |
|---|---|
| martensite | $6.6 \times 10^{-6}$/°C. ($3.67 \times 10^{-6}$/°F.) |
| Specific Heat | 0.20 cal/g · °C. (0.20 BTU/lb · °F.) |
| Corrosion Performance** | excellent |
| Electrical Properties | |
| Resistivity (ρ) | |
| [resistance = ρ · length/cross-sectional area] | |
| austenite | ~100 μΩ · cm (~39.3 μΩ · in) |
| martensite | ~80 μΩ · cm (~31.5 μΩ · in) |
| Magnetic Permeability | <1.002 |
| Magnetic Susceptibility | $3.0 \times 10^6$ emu/g |
| Mechanical Properties | |
| Young's Modulus*** | |
| austenite | ~83 GPa (~$12 \times 10^6$ psi) |
| martensite | ~28 to 41 GPa (~$4 \times 10^6$ to $6 \times 10^6$ psi) |
| Yield Strength | |
| austenite | 195 to 690 MPa (28 to 100 ksi) |
| martensite | 70 to 140 MPa (10 to 20 ksi) |
| Ultimate Tensile Strength | |
| fully annealed | 895 MPa (130 ksi) |
| work hardened | 1900 MPa (275 ksi) |
| Poisson's Ratio | 0.33 |
| Elongation at Failure | |
| fully annealed | 25 to 50% |
| work hardened | 5 to 10% |
| Hot Workability | quite good |
| Cold Workability | difficult due to rapid work hardening |
| Machinability | difficult, abrasive techniques are preferred |

*Values listed are for a full martensite to austenite transition. Hysteresis can be significantly reduced by partial transformation or ternary alloys.
**Similar to 300 series stainless steel or titanium
***Highly nonlinear with temperature
[1]Design News, June 21, 1993 issue, p. 77.

All the different specific formulations and metallic blends comprising nickel and titanium which yield a deformable, thermoelastic, shape-memory alloy composition are suitable for use when practicing the present repair methodology. All of these shape-memory alloys rely on a crystal phase change from a higher temperature Austenite form to a lower temperature Martensite form to accomplish the memory effect. The cubic Austenite phase behaves much like ordinary metals as it deforms. In contrast, the complex crystal Martensite form can beformed by reversible movement of twin boundaries to change the average "tilt" or strain in each segment of the alloy. The overall strain can be eliminated by releasing the stress, by maintaining it if it is not thermally stable (the superelastic effect), or by heating the alloy to change it back to Austenire form (shape-memory effect).

The crystal transformation of shape-memory alloy compositions is, by definition, thermoelastic—i.e., it progresses in one direction on cooling below the transition temperature and in the other direction upon heating above the transition temperature. The amount of transformation change versus temperature, measured either as the percent of Martensite form or the strain in a constantly stressed element, is a function of and can be plotted against temperature (°C.) directly; and the change from one phase, (and identifiable shape) to another typically occurs in a narrow temperature range (often 5°–20° C.). Hysteresis takes place before the reverse transformation occurs.

The amount of strain accommodated due to the movement of twin boundaries, differs in each metallic alloy blending system. In the nickel-titanium system, for example, up to 8% reversible tensile strain is available; however, to guarantee a long life use, the strain is often limited to 4–5%.

The stress-strain behavior of shape-memory alloy compositions is employed to help explain the shape-memory effect. For instance, Martensite is much easier to deform than Austenite. Therefore, one can deform the alloy while cold with much less force than when heated to change it back into Austenire form. As a result, the alloy converts thermal energy to mechanical work at high forces.

Fixing the memory-shaped configuration in the metal alloy:

To prepare and fix the particular (or desired) shape to be "remembered" when the, alloy undergoes a temperature phase transition, the alloy composition (often termed "Nitinol metal") must be superheated initially to about 500° C. (or roughly 930° F.) for an hour while held in the fixed shape and position to be memorized. During this superheating process, the native alloy blend enters what is called the Austenite phase—a rigid lattice of nickel atoms surrounded by titanium atoms. Then, as the alloy metal cools below its transition temperature (which will vary with the percentage proportions of nickel and titanium), the alloy composition adopts the Martensite phase, in which the nickel and titanium atoms assume a very different arrangement—one that is very easy to bend and deform. Subsequently, when the deformed metallic alloy is reheated to the;. chosen transition temperature range between 25°–35° C., thermal motion causes the atoms to snap back into the Austenite phase, thereby restoring the fixed memory-shaped configuration of the object [Invention & Technology, Fall 1993, pages 18–23].

For purposes of practicing the present in-vivo repair methodology, it is most desirable that the shape-memory alloy composition be prepared in a metallic blend and formulation such that the temperature transition phase occurs at a temperature less than about 35° C., but greater than about 25° C.; and preferably be in the range from about 30°–35° C. This preferred 30°–35° C. transition phase temperature range is dictated by the demands of the human body which maintains a normal temperature at about 37° C. (98.6° F.); and typically shows a normal temperature range and variance of one two degrees Celsius above and/or below this normative temperature standard. It is for this reason that the broad temperature range be about 25°–35° C. and the preferred temperature transition occur in the range of 30°–35° C.; but that such transformation into the intended and fixed memory-shaped configuration occur at least by a temperature of 35° C. to insure a safety margin of medical usefulness.

The deformed-shape configurations of the alloy at temperatures less than 25°–35° C.

The deformed-shape configurations of the thermoelastic alloy composition at temperatures less than about 25°–35° C. (a temperature below its transition temperature at which the alloy exists in the Martensite phase) may take a broad variety of different lengths, diverse dimensions, and disparate overall configuration. Merely exemplifying the range and diversity of three-dimensional forms into which the thermoelastic alloy compositions can be deformed at temperatures below 25° C. are those illustrated by FIGS. 1A–1D and 2A–2D respectively. For purposes of practicing the present repair methodology, FIGS. 1A–1D are considered more preferred embodiments and constructions of the deformed-shape configured alloys, while FIGS. 2A–2D respectively represent formats and fabrications of the deformed alloy compositions in less frequently utilized configurations.

FIG. 1A shows a single wire strand 10 typically of 18–30 gauge thickness and having a length suitable to meet the requirements of the particular application or use circumstance. FIG. 1B illustrates a three wire strand 16 intertwining embodiment and represents those instances where multiple wire strands are desirably intertwined to provide both bulk and strength. In comparison, FIG. 1C shows a substantially planar thin (18–30 gauge), narrow width (typically 1–3 millimeters), elongated bar 20 of predetermined length to suit the use circumstances. In comparison, FIG. 1D shows a substantially planar ribbon 30 of metallic alloy composition which is relatively thin (180 gauge), broad (typically 3–5 millimeter in width), and also is of a chosen axial length suitable to meet the required circumstances. Thus, while the various embodiments of the alloy may be termed "wire strands", or "twisted cable", or a "bar", or a "ribbon", or a "strip", or any other configuration described directly or inferred herein, the preferred universal collective term inclusive of any or all of these shaped formats and embodiments of alloy composition herein will be termed "rods". Accordingly, the nomenclature and use of the word "rod" hereinafter will signify, describe, define and delineate any thermoelastic, shaped-memory alloy composition of predetermined dimensions which has an identifiable deformed-shape first configuration at temperatures less than about 25°–35° C.—while being able to transform into a previously fixed memory-shaped, second configuration at temperatures greater than about 25°–35° C. Included within this vocabulary are all the configurations illustrated by FIGS. 1–6 respectively, as well as any other distinct form, shape, pattern, fashion, or spatial characteristic possible for metallic alloys generally. Thus, regardless of whether the specific shape or configuration is regular or irregular, symmetrical or asymmetrical, geometric or non-geometric, coherent or non-coherent, and patterned or random, all of these dimensional particulars and form specifics are encompassed and bounded within the phrase "elongated metal rod".

Given this terminology, FIGS. 2A—2D illustrate several different deformed-shape configurations commonly existing at temperatures less than about 25°–35° C. for limited or specific applications and use circumstances. As seen herein, FIG. 2A shows three parallel wire strands bound together by a coiled fourth wire strand wound in a perpendicular axis to form a stranded cable 90. In comparison, FIG. 2B illustrates a hollow, tubular filament 92 of predetermined length formed of the alloy composition. Alternatively, FIG. 2C shows a strip 94 of metallic alloy whose sides are patterned in curves in a regular, symmetrical orientation. Finally, FIG. 2D shows a multi-sided housing 96 having an internal volumetric channel and deformable side walls. The construction and utility of these elongated metal rods formed of shaped-memory alloy compositions is intended to meet specific types of fractures, fissures, and deformities in a therapeutic appliance whose particular requirements demand these specific structural forms as a first-shaped configuration in order to mend and repair the fragment or rupture.

The memory-shaped fixed configuration at temperatures greater than about 25°–35° C.

It is an essential and absolute requirement of the present in-vivo repair method that the elongated metal rod formed of a shape-memory alloy composition be able to transform into a second fixed configuration at temperatures greater than about 25°–35° C. from the deformed-shaped configuration appearing at temperatures less than about 25°–35° C. This second memory-shaped fixed configuration occurs at elevated temperature zones (greater than about 25°–35° C.); and the thermal energy of the elevated temperature (above the transformation temperature) causes the atoms of the alloy composition to transform into the Austenite phase-thereby restoring and regenerating the desired memory-shaped format created and fixed during the initial superheating processing (occurring at about 500° C.). Thus, for purposes of practicing the present repair methodology, the transforming temperature at which the thermoelastic elongated metal rod becomes transformed into the fixed, memory-shaped second configuration occurs at or near substantially normal body temperatures (within a medically permissible range). It is the transformation into this fixed, memory-shaped second configuration which provides the repair capabilities for mending the flawed therapeutic appliances in-vivo.

The fixed, memory-shaped configuration for the alloy composition can alternatively take the form of circles, ovals, helixes, and spirals-all of which are substantively round in measurable degree; or can appear as a series of flexed contractions along an axis or seam to form essentially a "V" or "U" shaped channel housing; or take form in any combination of these as desired or required to meet particular application or unique use circumstances. It will be recognized and understood that a wide and diverse range and variety of fixed memory-shaped second configurations can be prepared in advance via the conventional superheating preparation process for the thermoelastic alloy compositions; and that any or all of these fixed memory-shaped configurations are within and encompassed by the scope of the present invention without regard to whether these are symmetrical or asymmetrical, patterned or random, regular or irregular, and coherent or non-coherent. Presented merely as illustrative examples of some preferred memory-shaped configurations generally deemed to be useful in the repair process and technique are those illustrated by FIGS. 3–6 respectively.

The transformation of a deformed-shape configuration into a fixed memory-shaped configuration:

The transformation of a thermoelastic metal alloy from a first deformed-shape configuration (existing at temperatures less than 25°–35° C.) into a specific, prepared-in-advance, fixed memory-shaped configuration (at temperatures greater than about 25°–35° C.) is an essential and critical event for practicing the present repair methodology. This transformation event is represented and illustrated by FIGS. 3–6 respectively. It will be clearly understood, however, that the specific configurations of FIGS. 3–6 are merely visual examples of some preferred embodiments; and that the illustrated deformed-shape configurations and fixed memory-shaped configurations do not limit nor restrict the range or the variety of individual forms able to undergo transformation as a consequence of a change in temperature.

As shown therein, FIGS. 3A–3D illustrate the transformation of a single wire strand 10 from a first deformed-shape configuration at a temperature less than 25°–35° C. and its transformation into a fixed memory-shaped second configuration at an elevated temperature greater than 25°–35° C. FIG. 3A shows the single wire strand 10 as an elongated metal rod at the lower temperature range as it approaches the temperature boundary axis EE'. Clearly, the first deformed-shape configuration is a substantially straight elongated wire strand within the less than 25°–35° C. temperature environment. Nevertheless, as the temperature boundary threshold along the axis EE' is passed and the wire strand enters the elevated temperature zone greater than 30°–35° C., the wire strand is transformed (or transmuted) into the fixed memory-shaped second configuration and forms a spiral loop 12 which is oriented in a right-hand direction. Moreover, as shown by FIG. 3C, as the wire strand 10 is extended further into the elevated temperature zone greater than 30°–35° C., the wire strand continues to coil axially along its length as the alloy composition enters the elevated temperature zone and a second spiral loop 12b is generated in addition to the earlier formed spiral loop 12a. Moreover, as shown by FIG. 3D, as ever greater axial lengths of the wire strand 10 enter the elevated temperature zone greater than 25°–35° C., an entire series of parallel spiral loops 12 are formed, which collectively generate a discrete helix structure 14 as the cumulative effect and result. The orientation of the helix 14 is as a series of right-handed spiral loops 12—all of which may be varied in diameter, number of coils forming the helix, and overall size of the resulting helix entity as forming the completed memory-shaped second configuration for the wire strand 10 within the elevated temperature environment.

Another illustrative example is provided by FIG. 4 which utilizes a thin, narrow bar format as the first deformed-shaped configuration at the lower temperature zone less than 25°–35° C. This is illustrated by FIG. 4A in which the alloy bar 20 appears entirely within the lower temperature zone (which is less than 25°–35° C.) but approaches the temperature boundary axis EE'. However, as shown by FIG. 4B, once the planar bar 20 passes through the temperature boundary axis EE' into the elevated temperature zone greater than 25°–35° C., the alloy substance of the bar 20 begins to coil and form a spiral loop 22 in a left-handed orientation relative to the point of entry. Then, as shown by FIG. 4C, when the planar bar 20 is extended further into the elevated temperature zone greater than 25°–35° C., the alloy composition further continues to coil and spiral thereby forming a second spiral loop 22b in addition to the initially formed spiral loop 22a. This transformation (or transmutation) process continues to proceed further as the planar bar 20 enters farther into the elevated temperature zone. Thus, as shown by FIG. 4D, the alloy composition continues to coil and form additional spirals such as third spiral loop 22c. The overall result of the temperature transformation process is the formation of a left-handed helical coil 24 formed of multiple spiral loops 22 from a single planar bar 20. The result is the collective and cumulative consequence of the narrow alloy bar 20 having entered the elevated temperature zone greater than 25°–35° C.

Another alternative memory-shaped fixed, second configuration and orientation is illustrated by FIG. 5 which utilizes a planar ribbon of alloy composition as the first deformed-shape configuration in the lower temperature zone less than 25°–35° C. As shown by FIG. 5A, the metal ribbon 30 has been prepared and pretreated (in the conventionally known manner) along a center line 32 which divides the width of the metallic ribbon 30 into two substantially equal halves 34a and 34b respectively. However, so long as the alloy ribbon 30 remains in the lower temperature zone less than 25°–35° C., the substantially flat planar form of the ribbon 30 is maintained indefinitely. Nevertheless, as show by FIG. 5B, once the alloy ribbon 30 passes the temperature boundary EE' and enters the elevated temperature zone greater than 25°–35° C., the alloy substance is transformed (or transmuted) into the fixed memory-shaped second configuration. The alloy composition is thus transformed along a seam 33 coincidental with the center line 32; and the width of the alloy ribbon becomes bent along the seam axis 38 into a "V" shaped format having two partially folded walls 36a and 36b which are spaced apart from each other at an acute angle and form an internal volumetric channel 38. As the alloy ribbon 30 is extended further into the elevated temperature zone greater than 25°–35° C., the result is shown by FIG. 5C in which the transformation process continues and the alloy composition is transmuted along its axial length into the fixed memory-shaped configuration of a "V" shape form having two partially folded side walls 36a and 36b and a discrete internal volumetric channel 38. The conclusion of the transformation event is illustrated by FIG. 5D in which the entire axial length of alloy ribbon 30 has been transformed into the fixed memory-shaped configuration within the elevated temperature environment greater than 25°–35° C.

A more sophisticated but particularly useful example of the progression of first deformed-shape configuration into a second memory-shaped fixed configuration is illustrated by FIG. 6 which employs a broad ribbon of thermoelastic deformable alloy composition. The sequence of events illustrated by FIGS. 6A–6D provides a elongated metal rod of alloy which is particularly suitable for repairing cracks, fissures, or breaks in structural valves, flanges, rimmed edges, or joined seamed structures. As illustrated by FIG. 6A, the alloy ribbon 40 is substantially planar within the lower temperature environment less than 25°–35° C.; and has a prepared center line 42 which divides the width of the alloy ribbon 40 into two substantially equal halves 44a and 44b along its axial length. However, as the alloy ribbon 40 passes through the temperature boundary axis EE' into the higher temperature zone greater than 25°–35° C., the width of the alloy ribbon folds along an axis 43 coincidental with the center line 42; and the ribbon halves 44a and 44b become folded toward each other along the axis 43 as curved sidewalls 46a and 46b. In addition, the axis 43 is itself bent from a linear orientation into a circular orientation; and in so becoming bent creates a circular internal volume 48 which is bounded by the curved sidewalls 46a and 46b and the axis 43. FIG. 6b shows the further continuation of the transformation process and the generation of the fixed memory-shaped configuration in ever-increasing degree. Thus, FIG. 6C shows the near completion of the transmutation process and the phase transformation into the memory-shaped second configuration; while FIG. 6D shows the competed and fully transformed memory-shaped configuration as a circular ring having two folded side walls 46a and 46b at an acute angle relative to one another, and a discrete "U" shaped circular internal channel volume 48. It will be readily recognized and appreciated that the circular ring format appearing as the fixed memory-shaped second configuration is most useful as a circular mending patch suitable for joining seams, flanges, rims, or the edges of two circular parameters together within the circular internal volumetric channel.

Other considerations for the thermoelastic metal alloy:

(1). The various nickel and titanium formulations conventionally known for the thermoelastic metal alloy compositions used herein have the advantage and benefit of being biocompatible with living human cells, tissues and organs. These metal alloys are demonstrably non-toxic, non-hazardous, and safe for use as implantable materials in-vivo without fear of eliciting or inducing adverse biological reactions.

(2). If desired for specific use circumstances and particular applications, the thermoelastic metal alloy compositions (comprised of nickel and titanium metals) can be covered partially or completely with one or more non-metallic coating compounds to further enhance their biological inertness and/or to increase the speed of the healing process in-vivo after the repair has been successfully concluded. Thus, any or all of the conventionally known coating compounds typically employed for these enhancement purposes can be employed. These include but are not limited to the following: pyrolite carbon coatings of varying formulation; resilient synthetic polymers such as the various polyethylenes (e.g. tetrafluoropolyethylene or "TEFLON"), polyurethanes, and polyacrylates; diverse biological materials such as collagen, fibronectin, and albumin from varying sources; and any other natural or synthetic compound, formulation, or product having well demonstrated and recognized in-vivo coating properties.

(3). The thermoelastic metal alloy compositions, whether coated or uncoated prior to use, are expected to cause and elicit the formation of deposits in-vivo after the repair to the therapeutic appliance has been made. A range of biological deposits are expected to form over and around the repair site in-vivo; and these in-vivo created deposits will typically take form as fibrin, collagen, and other biologically created materials—all of which aid and speed the healing process. Thus, after the repair has been concluded via the present methodology, the in-vivo deposition of these biological materials over and around the repair site itself will both augment and increase the quality of the repair over time as part of the normal continuing life processes.

(4). The present methodology provides a durable in-vivo repair of a previously implanted therapeutic appliance which will last for an indefinite period of time. Thus, the repair can be a temporary solution if the therapeutic appliance is itself to be used in-vivo on a limited time or function basis; or, alternatively, can be a permanent repair lasting for the remaining life of the patient—depending on the patient's need for the therapeutic appliance originally.

II. The Flexible Guiding Catheter

The in-vivo repair method comprising the present invention requires that a controlling or guiding flexible catheter be employed as an essential part of the manipulations. This controlling or guiding flexible catheter has at least one tubular wall of fixed axial length; has at least one proximal end for entry; has at least one distal end for egress; and has at least one internal lumen of a volume sufficient to allow for on-demand controlled passage therethrough of the elongated thermoelastic metal rod (in the deformed-shape configuration).

Catheters, particularly surgical catheters, are conventionally known and used; and a wide range and variety of guiding catheters are available which are extremely diverse in shape, design, and specific features. All of the essential requirements of a guiding flexible catheter exist as conventional knowledge and information in the relevant technical field; and all of the information provided in summary form hereinafter is publicly known, widely disseminated, and published in a variety of authoritative texts. The reader is therefore presumed to be both familiar with and have an in-depth knowledge and understanding of the diagnostic and therapeutic uses of catheters and catheterization techniques. Merely representative of the diversity of publications publicly available are the following, each of which is expressly incorporated by reference herein: Diagnostic And Therapeutic Cardiac Catheterization, second edition (Pepine, Hill, and Lambert, editors) Williams & Wilkins, 1994 and the references cited therein; A Practical Guide To Cardiac Pacing, fourth edition (Moses et. al., editors) Little, Brown, and Company, 1995 and the references cited therein; Abrams Angiography, third edition (H. L. Abrams, editor), Little, Brown & Co., 1983.

A number of specific types of controlling or guiding catheters are known today; but for purposes of practicing the present invention, a number of newly designed or specifically designed catheters of varying lengths and sizes able to meet specific type-.; of flaws or ruptures in a therapeutic appliance are expected and intended to be developed and manufactured. Equally important, minor modifications of the presently existing general categories of catheter type are equally appropriate and are expected to be found suitable for use when practicing the present methodology. Accordingly, a summary review of the conventionally known catheter types as well as general catheter design and the principles of catheter construction are presented herein.

Catheter construction and design:

Presently known specific types of catheters include the following: central venous catheters which are relatively short (usually 20–60 centimeters) in length and are designed for insertion into the internal jugular, subclavain, or antecubital vein; right heart catheters such as the Cournand catheter designed specifically for right heart catheterization; transseptal catheters developed specifically for crossing from right to left atrium through the interatrial septum at the fossa ovalis; angiographic catheters which are ventricular catheters and are frequently used today in the femoral or brachial approach for right or left ventriculography and angiography in any of the major vessels; coronary angiographic catheters which include the different series of grouping including Jones, Judkins, Amplatz, multipurpose, and bypass graft catheters; as well as many others developed for specific purposes and medical conditions.

Figure 8:
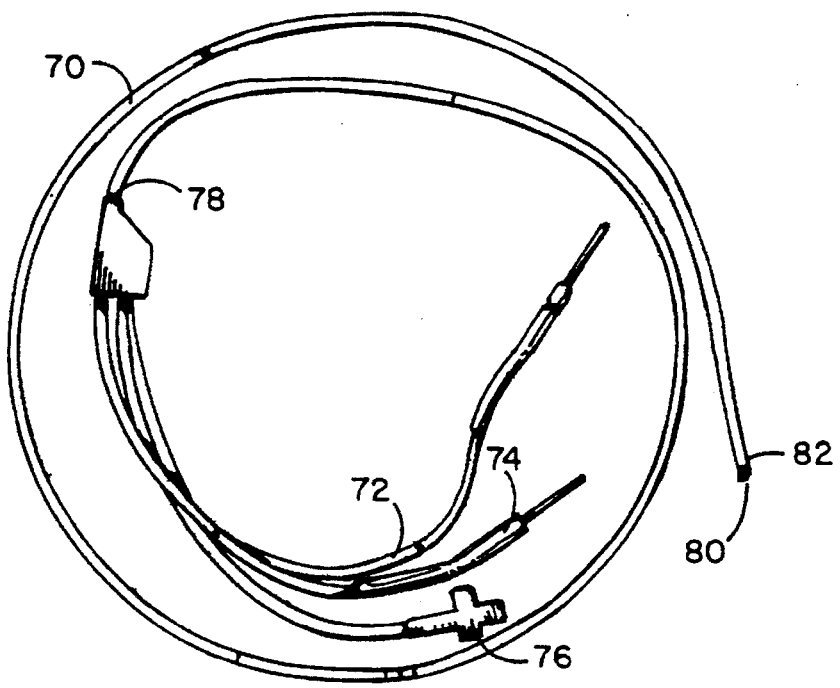
FIG. 8 is an overhead view illustration of another conventionally known guiding catheter.

Merely representative of guiding and controlling flexible catheters, generally presented herein without regard to their specific past usages or intended applications, are those illustrated by FIGS. 7 and 8 respectively. As exemplified by the catheter of FIG. 7, a catheter 50 is seen having a tubular wall of fixed axial length; having two proximal portals 52 and 54 which together generate the proximal end 56 for entry into the interior of the catheter 50; a single distal portal 58 and the distal end 60 of the catheter 50; and an internal lumen 62 (which is not visible in the illustration).

Another variation commonly known is illustrated by FIG. 8 which shows a controlling flexible catheter 70 having a tubular wall of fixed axial length; three proximal portals 72, 74, and 76 respectively which collectively form the proximal end 78 for entry into the internal lumen of the catheter; and a single distal portal 80 which designates the distal end 82 or tip of the catheter. It will be appreciated and understood that FIGS. 7 and 8 are presented merely to show the overall general construction and relationship of parts present in each flexible controlling catheter suitable for use with the present methodology.

In accordance with established principles of conventional catheter construction, the axial length of the catheter may be composed of one or several layers in combination. In most multilayered constructions, one hollow tube is stretched over another to form a bond; and the components of the individual layers determine the overall characteristics for the catheter as a unitary construction. Most multilayered catheters comprise an inner tube of Teflon, over which is another layer of nylon, woven Dacron, or stainless steel braiding. A tube of polyethylene or polyurethane is then heated and extruded over the two inner layers to form a firm bond as the third external layer. Other catheter constructions may consist of a polyurethane inner core, covered by a layer of stainless steel braiding, and a third external jacket layer formed of polyurethane.

Several examples of basic catheter construction and design are illustrated by FIGS. 9-12 respectively. FIGS. 9A and 9B are perspective and cross-sectional views of a single tubular wall considered the standard minimum construction for a catheter. FIGS. 10A and 10B are perspective and cross-sectional views of a thin-walled design for a single layer extruded catheter. In comparison, FIGS. 11A and 11B are perspective and cross-sectional views of a standard multi layered catheter construction having a braided stainless steel midlayer in its construction. Finally, FIGS. 12A and 12B are perspective and cross-sectional views of a thin-walled design for a multilayered catheter with a braided stainless steel middle layer.

Catheters are generally sized by external and internal diameter and length. The internal diameter specified either by actual diameter (in thousandths of an inch or millimeters or French). Many newer thin-walled catheter designs provide a much larger internal lumen volume to external diameter ratio than has been previously achieved; this has resulted in catheters which can accommodate much more volume and allow the passage of much larger sized articles through the internal lumen. External diameter is typically expressed in French sizes which are obtained by multiplying the actual diameter of the catheter in millimeters by a factor of 3.0. Conversely, by traditional habit, the actual size of any catheter in millimeters may be calculated by dividing its French size by a factor of 3.0. French sizes from 5–8 are currently used for diagnostic angiography. For purposes of practicing the present invention, it is also desirable that French sizes ranging from 5–8 respectively be employed unless other specific size requirements are indicated by the particular application or circumstances. In addition, because of the variation between standard, thin-walled, and super high-flow catheter construction designs, a range and variety of external and internal lumen diameter sizes exist. To demonstrate the conventional practice, the data of Table 2 is provided.

TABLE 2

External and Lumen Diameter Measurements in Standard, Thin-Walled, and Super High-Flow Diagnostic Catheters

| French Size | External Diameter inches | External Diameter mm | Standard (High Torque) inches | Standard (High Torque) mm | Thin-Walled (High Flow) inches | Thin-Walled (High Flow) mm | Super (High Flow) inches | Super (High Flow) mm |
|---|---|---|---|---|---|---|---|---|
| 5 | 0.065 | 1.67 | a | a | 0.044 | 1.08 | 0.052 | 1.28 |
| 6 | 0.078 | 2.00 | a | a | 0.050 | 1.27 | 0.056 | 1.42 |
| 7 | 0.092 | 2.34 | 0.048 | 1.22 | 0.056 | 1.42 | 0.061 | 1.55 |
| 8 | 0.104 | 2.64 | 0.056 | 1.42 | 0.063 | 1.60 | a | a |
| 9 | 0.118 | 3.00 | a | a | a | a | a | a | aNo catheters made in this size/type.

In general, the tubular body of the catheter is generally straight over most of its length and may have different bends or curves towards the distal end or tip. A representative illustration of the distal end of a catheter is illustrated by FIG. 13. The individual bends in the catheter are traditionally called "curves"; and the terms "primary, secondary, etc.," are applied to each additional curve further away from the distal tip as is illustrated by FIG. 13. Accordingly, the primary curve 100 is followed by the secondary curve 102, which in turn extends into the catheter body 104 generally. The catheter tip 106 is its most distal segment. In addition, the catheter distal tip 106 may have any combination of a single end hole (not shown) or a closed distal end 108 and any number of side holes 110 which function as portals for exiting the distal end of the catheter.

Conventional practice permits a number of different distal ends or tips which vary in design and appearance. As merely a representative illustration of these permitted and conventional variances in distal end design for catheters generally, the distal ends of four ventricular catheters are illustrated by FIG. 14. Distal end 14A of FIG. 14 is a "pigtail" design and construction which has a curled-tip format and multiple side holes. In comparison, distal end 14B is a Lehman ventricular catheter end which provides a number of side holes in different places along the distal end. Similarly, distal tip 14C is recognized as the NIH version while distal end 14D is known as the Gensini design which provides multiple side holes at varying angles. Accordingly, for purposes of practicing the present repair methodology, any construction of the catheter distal end whether having one or more curves, or none; and whether or not there is a central portal for exiting the lumen or multiple side holes only with a closed distal tip are all considered conventional variations in construction design. Any and all of these distal tip designs and construction are therefore deemed to be encompassed completely and to lie within the general catheter scope of construction suitable for use with the present methodology.

Dual-lumen catheters

A number of different dual-lumen catheters are known today which differ in the size and spatial relationship between their individual lumens. This is illustrated by FIGS. 15A–15D respectively which show different dual-lumen constructions for four catheters having similar or identical overall diameter (French) size.

Figure 15A:
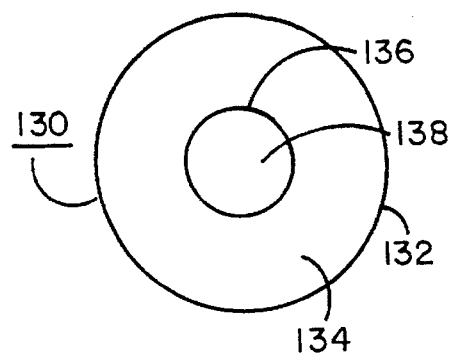
FIGS. 15A–15D are cross-sectional illustrations of four different constructions and designs for dual-lumen catheters.

As shown therein, FIG. 15A shows a dual-lumen catheter 130 wherein a first external tubular wall 132 provides an outer lumen volume 134 into which a second internal tubular wall 136 has been co-axially positioned to provide an inner lumen volume 138. Clearly, the construction of catheter 130 is a co-axial design of multiple tubular walls paced apart and co-axially spaced but separated internal lumens of differing individual volumes.

Figure 15B:
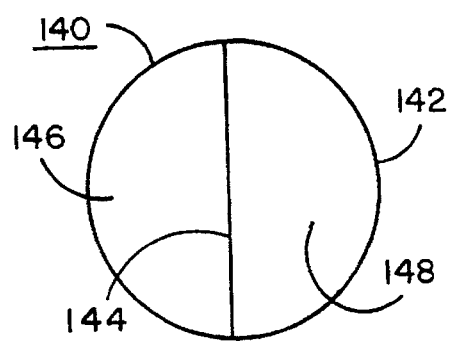

In comparison, FIG. 15B shows a second kind of construction and design by dual-lumen catheter 140 having a single external tubular wall 142; and a centrally disposed inner septum 144 which divides the interior tubular space into two approximately equal lumen volumes 146 and 148 respectively. Thus, in this construction, the diameter, length, and volume of internal lumen 146 is effectively identical to the diameter, length and volume of internal lumen 140; and both of these exist and are contained within a single, commonly-shared, tubular wall.

Figure 15C:
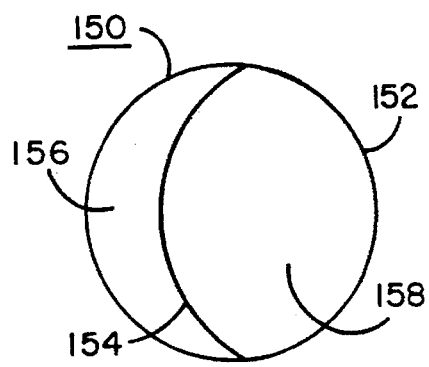

A third kind of construction is illustrated by FIG. 15C and shows an alternative kind of construction and design to FIG. 15B. As seen in FIG. 15C, dual-lumen catheter 150 has a single external tubular wall 152; and contains an asymmetrically positioned internal divider 154 which divides the interior tubular space into two unequal and different lumen volumes 156 and 158 respectively. Thus, in this alternative construction, the discrete volume of internal lumen 156 is markedly smaller than the volume of the adjacently positioned internal lumen 158; and yet both of these internal lumens 156 and 158 exist in parallel, are adjacently positioned, and are both contained within a commonly-shared single tubular wall.

Figure 15D:
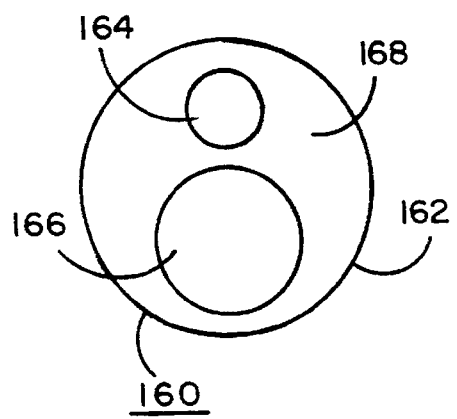

A fourth construction and design for a dual-lumen catheter is presented by FIG. 15D which shows a catheter 160 having a single external tubular wall 162 of relatively large size and thickness. Within the material substance 168 of the tubular wall 160 are: two discrete bore holes 164 and 166 of differing diameters which serve as two internal lumens of unequal volume. Internal lumen 164 is clearly the smaller while internal lumen 166 is far greater in spatial volume. Yet each internal lumen volume 164 and 166 is adjacent to the other, lies in parallel, and follows the other over the axial length of the catheter.

Maintaining the environmental temperature of the internal lumen of a catheter at less than about 25°–35° C.

The preferred means for cooling and maintaining the temperature of an internal lumen in a guiding catheter at less than about 25°–35° C. during the process of making an in-vivo repair to an implanted therapeutic appliance is via the use of cold physiological-strength (0.85–0.9%) saline. Typically, a sterile saline pack is refrigerated in advance of the repair surgery and cooled to a temperature between 40°–50° F. (5°–10° C.). The cooled saline is then infused by the surgeon or radiologist into one or more internal lumens of the catheter in order to cool the internal lumen volume both initially and periodically during the surgery. The sterile saline is compatible with the living tissue of the patient; and multiple applications of saline can be introduced into the internal lumen volume of the catheter as often as deemed necessary without meaningful risk to either the repair procedure or the health of the patient.

As an alternative to the use of saline infusion, any other suitable means for cooling may also be employed as a less preferred practice for maintaining the environmental temperature of the internal lumen volume of a catheter at less than about 25°–35° C. Such alternative procedures, however, are usually far less desirable due to the effects of potential direct contact and possible biological reaction when intentionally or inadvertently released into the bloodstream or other highly vulnerable organs and tissues of the body. Nevertheless, the use of alternative means to reduce the environmental temperature of the internal lumen volume of a catheter to less than about 25°–35° C. can be safely and properly performed in many different medical circumstances where the repair of a flawed or failing therapeutic appliance is made using the present invention.

III. The Routing and Surgical Introduction Of The Controlling Catheter Into The Body Of The Living Human The present in-vivo repair methodology is a general purpose technique intended to be usefully employed for the repair of a flawed or failing therapeutic appliance located, implanted or positioned anywhere within the body of a living human. The present repair methodology thus does not discriminate as to where the ruptured or fragmented therapeutic appliance may be found so long as it exists in-vivo; and the present repair method is appropriate for use with any and all organs, tissues, ducts, canals, and internal systems-so long as that zone, area, or locale can be accessed using generally known and conventionally used catheterization techniques.

Catheterization involves a great deal of technical skill, some instrumentation and mature judgment in order to choose among the appropriate procedures and the various techniques which are now conventionally known and available for use. Clearly, because the present repair technique constitutes catheter intervention in critically ill patients, the physician or surgeon must be very familiar with the available anatomical alternatives in order to select the best routing for introducing the catheter, the best technique in order to access the area of the body where the ruptured therapeutic appliance exists, and to carefully select the timing and other operative conditions in order to achieve best results.

Catheterization can be performed using any duct, tube, channel, or passageway occurring naturally or surgically created for the specific purpose. Thus, among the naturally occurring passageways are the anus; the alimentary canal; the mouth, ear, nose, or throat; a bronchus of the lung; a ureter; the vaginal canal and/or cervix; and any blood vessel of sufficient size of the central circulation in the body. Any of these routings are envisioned and expected to be used when and if appropriate. However, clearly the most commonly used and the most critical route of access is the introduction of catheters into the central blood circulation regardless of the location of entry.

For this reason, it is useful to briefly summarize the technique currently in use for introduction of catheters into the central blood circulation as an illustrative example of general catheterization techniques. There are two general methods currently in use. These are: (a) percutaneous introduction using needles and guidewires; and (b) direct introduction after surgical isolation of the blood vessel of choice. While either general method may be utilized at any site of the general circulation, practical and anatomical considerations including the site of the flawed therapeutic appliance will generally dictate which approach is most appropriate under the individual circumstances.

The modified Seldinger technique:

The percutaneous introduction of a catheter is best illustrated by the modified Seldinger technique which is shown by FIGS. 16A–16F respectively. FIG. 16A shows a blood vessel being punctured with a small gauge needle. Once vigorous blood return occurs, a flexible guidewire is placed into the blood vessel via the needle as shown by FIG. 16B. The needle is then removed from the blood vessel, the guidewire is left in place, and the hole in the skin around the guidewire is enlarged with a scalpel as shown by FIG. 16C. Subsequently, a sheath and a dilator is placed over the guidewire as shown by FIG. 16D. Thereafter, the sheath and dilator is advanced over the guidewire and directly into the blood vessel as shown by FIG. 16E. Finally, the dilator and guidewire is removed while the sheath remains in the blood vessel as illustrated by FIG. 16F. The catheter is then inserted through the sheath and fed through the blood vessel to reach the desired location.

The other general method for the introduction of catheters into the blood circulation is a direct surgical cutdown. The surgical cutdown approach is generally used for the brachial approach or the femoral approach. Cutdown procedure is often a complex surgery and is used only when no direct blood vessel access is generally available. A far more complete and fully descriptive review of both these general catheterization techniques is provided by the texts of: Diagnostic And Therapeutic Cardiac Catheterization, second edition, 1994, Chapter eight, pages 90–110 and the references cited therein.

Accordingly, for purposes of practicing the present in-vivo repair methodology, any and all conventionally known general catheterization procedures, apparatus, and techniques which are conventionally known and in accordance with good medical practice are explicitly intended to be utilized as necessary in their original format or in a modified form. All of these general catheterization routing and use techniques are thus envisioned and are deemed to be within the scope of the present invention.

General rules for choosing an appropriate site of body entry:

An axiomatic or general set of rules by which a surgeon or radiologist can choose a proper or appropriate site of entry for introducing the guiding catheter into the body of a patient for purposes of repairing a flawed therapeutic appliance in-vivo is as follows: (a) always pick the shortest and straightest pathway possible or available; (b) identify the patency of an existing and accessible vein, the larger the diameter of the vein the better; and (c) identify the location and orientation of the flawed or failing therapeutic appliance needing repair.

Preferred sites of entry on a general use basis:

In general, the preferred sites for introducing a guiding catheter into the body a patient are the (left or right) femoral or internal jugular veins. Veins typically provide, the best and easiest access route on the basis of the patient's build, the status of venous patency, and the location and orientation of the flawed or damaged therapeutic appliance. It is expected, however, that the right internal jugular approach and routing will be the most commonly chosen site of entry for repair of a cardiac pacemaker electrical lead since this vein provides a short and direct point of access to the pacer-electrode lead(s).

A favored approach to introducing the guiding catheter into the body:

Using the right internal jugular venous approach as a representative illustration and example:

(1). The right neck is prepared and draped in a sterile fashion.

(2). The skin over the right mid internal jugular vein is infiltrated with 1% lidocaine for local anesthesia.

(3). A small skin nick is made over the anesthetized area.

(4). Via the skin nick, the right internal jugular vein is punctured using a single wall puncture needle.

(5). A 0.035 inch or 0.038 inch guide wire is passed via the needle into the superior vena cava.

(6). A hemostatic 7–9 French introducer sheath is placed into the right jugular vein/superior vena cava.

(7). Via the hemostatic introducer sheath, the guiding catheter is passed and located next to the flawed or damaged therapeutic appliance.

IV. A Representative And Illustrative Problem Solved Using The Present Methodology In order to facilitate understanding of the present invention and to illustrate the utility and value of the in-vivo repair method as a generally useful procedure, a specific clinical problem involving a ruptured therapeutic appliance is presented hereinafter. It will be noted and appreciated, however, that this clinical example is presented merely as an illustration of the methodology and as a representative example of the many other different use circumstances for which the repair technique is functional and desirable. Under no circumstances, therefore, is the present invention to be limited or restricted to the specific clinical instance presented below.

Background of the problem

The patient is a living human who has a cardiac pacemaker previously implanted into the right side of the heart in order to control the electrical stimulation and contractions of the right atrium and right ventricle. The cardiac pacemaker lead is of the more modern and commercially sold type—that is, a pacing system having an J electrical lead which is joined to a programmable pacemaker and a lithium battery sealed in a package. In practice, the J-shaped pacing lead conducts electricity from the pacemaker generator to the heart; and this electrical circuit is joined to a programmable pacemaker connected to a lithium battery, which is itself sealed in a metal package and connected to a fitting for the pacing wire connector. This combination forms the complete pacemaker generator and J-retention wire and pacing lead comprising the entire cardiac pacing system implanted in-vivo. This is illustrated by FIGS. 17–21 respectively.

FIG. 17 shows a permanent J-retention wire pacing lead 200 of the screw-in type.. The pacing lead 200 comprises a screw housing 202, the insulated lead 204, a "J" shaped retention wire 206, and a styler 208. The screw housing 202 is shown in greater detail by FIG. 20. As shown, the screw-in lead can be used in either the ventricle or the atrium and is an active fixation lead. The J-retention wire illustrated in detail by FIG. 19 is part of a design commercially manufactured and sold by Teletronics Pacing Systems (Englewood, CO); and the function and purpose of the J-retention wits within the body of the electrical lead is solely to maintain the distal end of the pacing lead in a permanent fish-hook or J configuration during implantation of the electrical lead into the heart. The styler is used to guide the pacemaking lead into proper position against the heart wall and then is removed—leaving the J-retention wire holding the lead at the correct angle. The screws can then be turned so that they exit from the screw housing area and rum into the myocardium for permanent fixation.

The body of the permanent pacemaker lead 204 is illustrated in perspective cross-sectional view by FIG. 18. As shown therein, this bipolar lead has two electrodes "in line"; an outer ("proximal") electrode 220, and an inner (distal) electrode 222. Both the outer and inner electrodes are separated by individual layers of insulation 224. In this manner, the two electrodes are "coaxial", meaning that one electrode is coiled inside the other with insulation between them; and both the outer electrode and the inner electrode are individually insulated from the external environment.

The J-retention wire illustrated by FIG. 19 is typically about 3½ inches in length and formed of stainless steel such that a fish-hook shape or "J" configuration is maintained when the wire is bound to and united with the insulated body of the pacing lead. The J-retention wire was intended to be insulated from the external environment and, for this reason, was bound to the body of the pacing lead with insulation material. However, over time, it has been found that this J-retention wire can and does rupture through the insulation material and become exposed in-vivo openly as a bare and unprotected sharp wire fragment.

Figure 21:
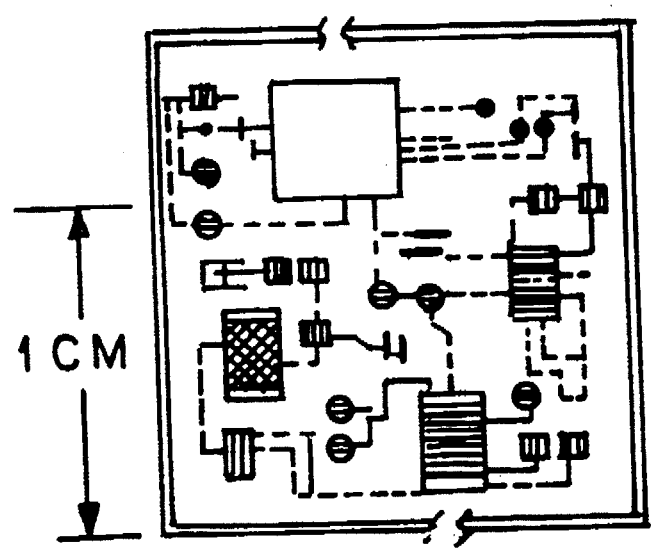
FIG. 21 is a diagrammatic view of an electrical circuit forming the cardiac pacemarker unit to be used with the pacing lead of FIG. 17.

The hybrid circuit of a typical programmable pacemaker is shown by FIG. 21. This circuitry will be connected to a lithium battery; sealed in a metal package; and connected to the J-retention wire pacing lead thereby forming the complete pacemaker system. The entirety of the lead and the electrical pacemaker circuitry is implanted within the living body.

The ruptured therapeutic appliance in-vivo:

The clinical problem arising from the use of J-retention wire pacing leads and pacemaker systems is illustrated by FIGS. 22A–22B and FIGS. 23A–23B respectively—all of which are fluoroscopic photographs showing a fractured J-shaped retention wire that has detached itself from the body of the pacing lead and clearly protruded through the outer insulation of the lead. FIG. 22A shows the lead at the imbedded distal end and its connections to the circuitry of the programmable pacemaker and the complete generator for the system. FIG. 22B shows the detail and the extent of rupture for the J-retention wire as it stands completely exposed and unprotected within the body. The exposed J-retention wire thus is a metallic spike or needle which can puncture, perforate, cut, or otherwise destroy the surrounding tissue, most notably the expanding and contracting heart chambers themselves. The danger to the patient is immediate, of the most serious and detrimental nature, and potentially is deadly. Clearly, the pacing lead has ruptured and has fragmented to expose the J-retention wire. The therapeutic appliance is thus flawed and clearly in need of repair.

Figures 24, 25:
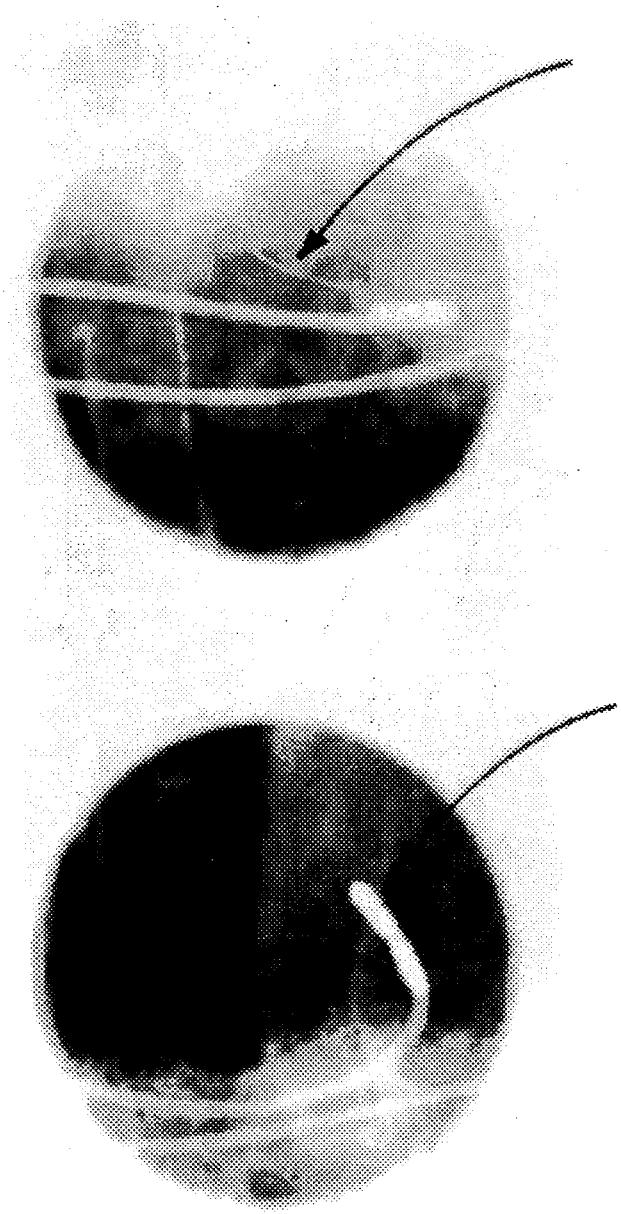
FIG. 24 is a fluorophotograph of the fragmented J-retention wire of FIGS. 22A and 22B showing a side view of the rupture.
FIG. 25 is a fluorophotograph of the fragmented J-retention wire of FIGS. 22A and 22B showing an overhead view of the rupture.
Figure 28A:
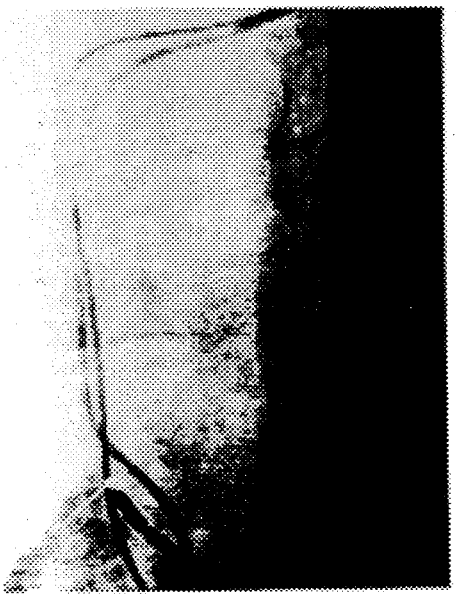
FIGS. 28A and 28B are fluorophotographs showing a fourth instance of a ruptured J-retention wire in a pacing lead existing in-vivo within a fourth living person.
Figure 28B:
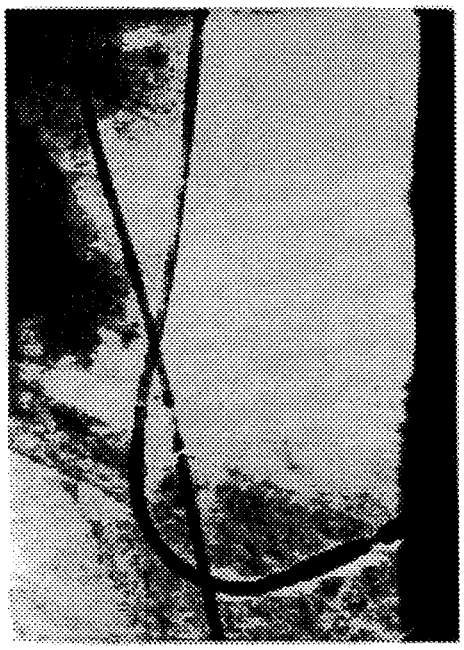
Figure 29A:
FIGS. 29A and 29B are fluorophotographs showing a fifth instance of a ruptured J-retention wire in a pacing lead existing in-vivo within a fifth living person.
Figure 29B:

Other fluoroscopic photographs illustrating alternative views of this broken J-retention wire defect in the pacing lead of a cardiac pacemaker are illustrated by FIGS. 24 and 25 respectively. The arrows in each figure indicate the clear presence of a fully exposed J-retention wire extending into the heart cavity in an unprotected and hazardous manner. The danger of heart or aorta puncture and other cardiovascular injury cannot be overestimated as a consequence. The risk of death to the patient and internal bleeding, all of which can be caused by this exposed J-retention wire defect cannot be minimized.

In addition, the fracture of the cardiac pacing lead and the exposure of the J-retention wire can and frequently does occur in different zones of the pacing lead. This is illustrated by FIGS. 26–29 respectively. As seen therein, FIGS. 26A and 26B illustrate a patient having an unusual "hinging" break in the pacing lead with a fracture of the J-shaped retention wire just distal to the "hinging" portion. The fracture of the J-retention wire is illustrated by the arrows. In comparison, FIGS. 27A and 27B each show a patient having a lead fracture in the distal third of the J-shaped retention wire which has perforated the outer insulation of the pacing lead. The fracture is illustrated by the arrows in each photograph. Alternatively, FIGS. 28A and 28B each demonstrate a patient having a pacing lead fracture in the middle third portion of the J-shaped retention wire that has a "volcano-like" lifting of the outer insulation. This lifting of the outer insulation is indicated by the arrows in these photographs. Finally, FIGS. 29A and 29B demonstrate a patient having a pacing lead fracture that has "tented" the outer insulation at the middle third portion of the J-shaped retention wire and has a "bulge" in the retention wire at the distal tip. These fractures are shown by the arrows in each of these photographs.

Figure 30:
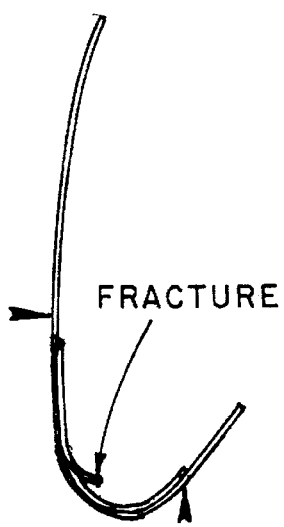
FIG. 30 is an illustration showing a first commonly occurring type fracture for a J-retention wire in a pacing lead.
Figure 31:
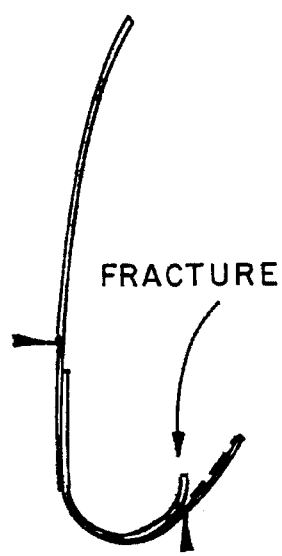
FIG. 31 is an illustration showing a second commonly occurring type of fracture for a J-retention wire in a pacing lead.
Figure 32:
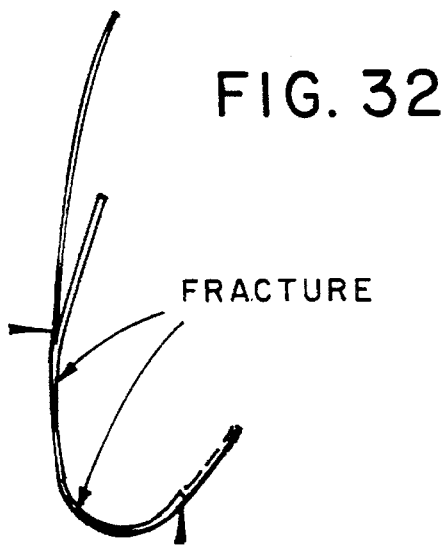
FIG. 32 is an illustration showing a third commonly occurring type of fracture for a J-retention wire in a pacing lead.

It has now been recognized and demonstrated that a variety of J-retention wire fractures with differing places of fracture, and alternative sites of rupture in the insulation material can and do occur in the pacing lead. Each of these is individually distinct and each of which demands individual attention and specific repair. Merely to illustrate further the range and variety of ruptures in the pacing lead and the different specific types of fractures of the J-retention wire as it protrudes from the pacing lead, FIGS. 30–32 are presented. In each instance illustrated by FIGS. 30, 31 and 32 respectively, the J-retention wire has broken free from the protective insulation encompassing the pacing lead; has fractured at an individual place into one or more fragments; and extends into the body cavity as a naked metal probe able to injure the surrounding heart and other tissues (such as the aorta) with each movement of the organ and body.

A preferred in-vivo repair technique

A. The Nitinol Metal Rod.

Nitinol metal ribbon is the preferred material for fixation of the electrode of the pacer with fractured J-retention wire. This metal alloy, composed of nickel and titanium I combined in a precise ratio, possesses a fixed and prepared shape-memory capability which takes form as a series of spirals or loops and collectively forms a coiled helix configuration. This memory-shape capability provides the ability of the material to regain its fixed and prepared shape completely when heated to a 25°–35° C. temperature. This phenomenon is based on thermal memory. This repair is desirably performed using a nitinol metal alloy rod prepared in fixed shape-memory in advance, and delivered through a guiding catheter.

B. The Delivery System.

The delivery system preferably utilizes a dual-lumen catheter constructed of two co-axially positioned tubular walls and two discrete internal co-axially spaced lumens, an outer ring lumen and an inner central lumen. The outer ring lumen volume serves to constrain and provide passage for the metal ribbon while the inner central lumen volume serves as the conduit and passway for a conventional anglographic guidewire. As the ribbon is gradually extended and is exposed to the warm-body temperature, it will resume its original coiled spiral loop shape to cover both the pacing lead and the fractured J-retention wire. The coil pitch of the spiral helix varies between tightly to loosely coiled depending on the fracture to be fixed.

C. Patient Preparation.

Candidates for procedures are seen prior to the examination. During this visit, the nature, benefits and risks of the procedure are explained and informed consent obtained. The peripheral pulses are evaluated. Routine laboratory evaluation includes blood urea nitrogen, creatinine, hematocrit-hemoglobin, PT, PTT, platelet count, and electrocardiogram.

Patients are restricted to a clear liquid diet beginning at least 8 hours prior to the procedure. Routine medications are not withheld on the morning of the examination. Administration of a sedative (Medazalam or Valium) and analgesic (Fentanyl or Demerol) medication are administered to the patients.

D. The Routine Technique For Repair.

(i). Using sterile technique, 2% lidocaine is infiltrated superficially to produce a wheal at the puncture site of the internal jugular view or the femoral vein. A small superficial incision is made A directly over the internal jugular vein or the femoral vein with a #11 scalpel blade and this opening is then widened with a hemostat to provide a space wide enough to accept the designated catheter.

(ii). The needle is placed through the skin nick and then advanced at a 45°–60° C. angle. The styler is removed and the needle is withdrawn with gentle aspiration until venous blood is obtained.

(iii). The guide wire is advanced under fluoroscopic control into the inferior vena cava.

(iv). The needle is exchanged for a vessel dilator. The purpose of the dilator is to form a tract to facilitate subsequent passage of the softer and larger introducer sheath for which it is subsequently exchanged.

The guiding catheter of the delivery system is advanced over the guide wire into the superior vena cava just next to the electrode lead (atrial) of the pacer. Using fluoroscopic guidance and contrast injections, the metal ribbon is extended and released into the heart chamber. The released metal ribbon, upon being exposed to normal body temperature, will form one spiral loop at a time and thus create a coiled helix over the fragmented &retention wire and the body of the pacing electrode lead.

The cumulative and collective result of performing the in-vivo repair methodology such that a fractured J-retention wire becomes reattached and molded to the body of the pacing electrode lead is illustrated by FIGS. 33A–33D respectively. As seen within FIG. 33A, a pacing electrode lead 300 is shown from which the J-retention wire 302 has ruptured through the insulation and appears as an exposed fragment 304. A guiding dual-lumen catheter having co-axial outer ring and inner central lumens (not shown) and distal portal or side holes 312 has been positioned adjacent to the pacing electrode lead 300 and the J-retention wire 302. The co-axial internal lumens of the guiding catheter 310 contain cold saline and a deformed-shape metal ribbon which has been pre-prepared to form spiral loops and take helical shape when transformed into a temperature environment greater than about 25°–35° C. The shape-memory metal rod 320 is shown extending from a side hole 312 of the guiding catheter 310 and begins to form the first spiral loop as it transforms into the pre-prepared fixed memory-shaped configuration.

Figure 33A:
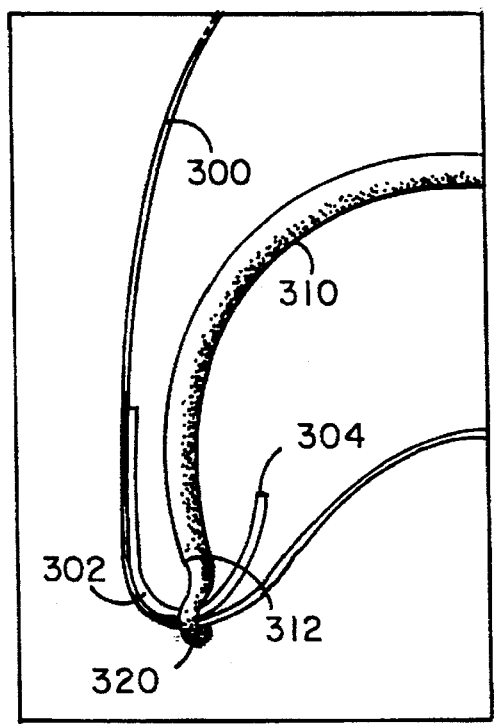
FIGS. 33A–33D are sequential illustrations showing the repair of a fragmented J-retention wire in a pacing lead using the present invention.
Figure 33C:
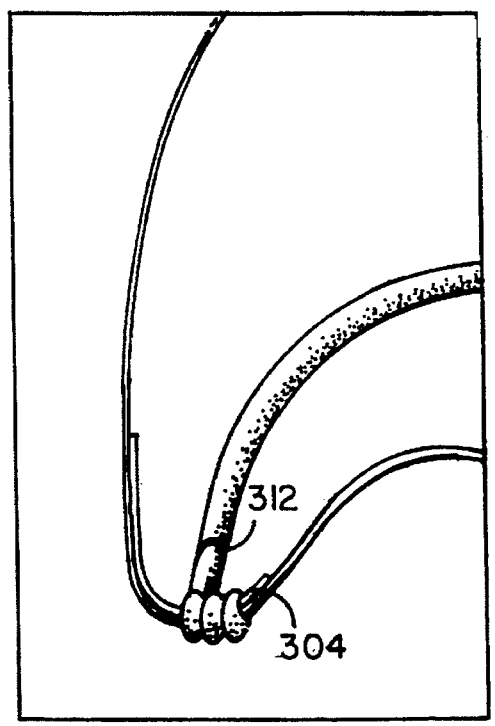
Figure 33B:
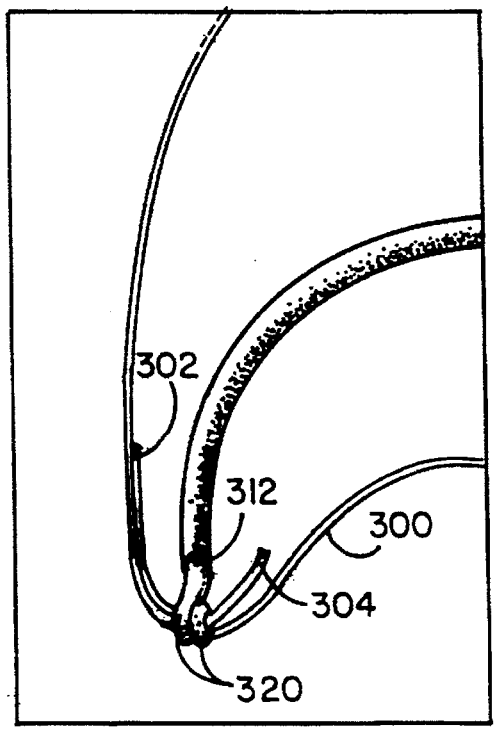
Figure 33D:
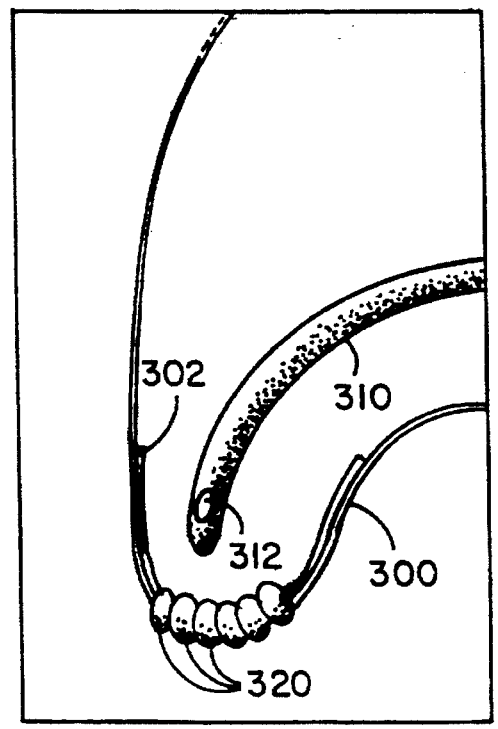

The extension of the metal rod 320 is continued as shown by FIG. 33B. As seen therein, a second spiral coil has been formed by the metal rod 320 as it is further extended through a side hole 312 of the dual-lumen catheter 310. FIG. 33C continues the repair technique and shows a third spiral loop alloy metal 320 having been formed as a consequence of the metal alloy ribbon being further extended through one internal lumen of the guiding catheter. Finally, FIG. 33D shows the completed repair and a complete reattachment of the exposed wire fragment 304 to the body of the electrode lead 300 as a consequence of the spiral loops and helical coiling of the alloy metal 320. It will be seen also by FIG. 33D that the entire fragmented J-retention wire can be overlayed completely, encircled, and encompassed by the alloy metal 320 at will in one or more layers. Thus, the illustration and result of FIG. 33D is only one of several repair formats which may be utilized at the surgeon's discretion and choice.

V. Other In-Vivo Repair Instances And Applications

It will be recognized and appreciated that the present in-vivo repair methodology is expected and intended to be employed in a wide variety of applications and use circumstances in which a flawed therapeutic appliance exists within the body of a living patient. The detailed disclosure of the J-retention wire repair in the cardiac pacemaker lead is merely one instance, albeit a currently important example, of repairs being made in-vivo. A great variety and diverse range of other applications and repair usages is envisioned and deemed to be within the scope of the present invention. A representative, but non-exhaustive listing, is provided by Table 3 below.

TABLE 3

| Type | Examples(s) |
|---|---|
| A. Prosthetic Devices | |
| Structural | Skull plate |
| | Head of femur bone |
| | Nail/spike anchors |
| Mechanical Connectors | Synovial joint replacement |
| | Pelvic girdle |
| | Heart valves |
| | Inner ear connectors |
| B. Physiological-Assist Articles | |
| Structural | Vascular stents |
| | Vascular patches |
| | Synthetic septum |
| Mechanical-flow Units | Blood filters |
| Electrical | Cardiac pacemakers |
| | Pacing electrode leads |
| Electro-Mechanical | Artificial heart chambers |
| | Ventricular assist pumps |

It is also desirable to identify some more specific instances in which the present repair methodology can and will be of major value as a repair technique. For example: in the brain, to repair and mend a broken stainless steel clamp on an aneurysm; in an artery, to be able to reinforce stents which have become weakened or even fragmented through long-term use; with prosthetic valves, to create and mend a broken valve flange or seam; in the heart, to serve as a means for refastening of the stitching for a previously implanted heart valve prosthesis; in a vein, to repair a fragmented venous shunt; in the inner ear, to repair a preexisting stent for eustation tubes; and in a bone, to repair synthetic coverings for the damaged heads of large bones such as the femur. It will be acknowledged and noted that this listing is merely an illustrative and exemplary recitation representative of many different kinds of problems well-established and recognized in the medical areas of orthopedics, radiology, and cardiology. Any and all of these are therefore within the scope of the present methodology.

The present invention is not to be limited in scope nor restricted in form except by the claims appended hereto.

What we claim is:

1. An in-vivo method for repairing a ruptured segment of a therapeutic appliance which has been previously surgically positioned within the body of a living human, said in-vivo repair method comprising the steps of:

providing at least one metal alloy rod of predetermined dimensions and comprised of a deformable thermoelastic shape-memory alloy, at least a portion of said thermoelastic metal rod being substantially in a first deformed-shape configuration at temperatures less than about 25°–35° C. while transforming into a memory-shaped second configuration at temperatures greater than about 25°–35° C.;

providing a controlling flexible catheter having at least one tubular wall of set axial length, at least one proximal end for entry, at least one distal end for egress, and at least one internal lumen of a volume sufficient to allow for on-demand controlled passage therethrough of said thermoelastic metal rod;

surgically introducing a portion of the axial length of said controlling flexible catheter into the body of the living human such that said distal end of said surgically introduced catheter becomes positioned adjacent to the ruptured segment of the therapeutic appliance in-vivo;

maintaining at least a portion of said internal lumen of said surgically introduced catheter at a temperature less than about 25°–35° C.;

placing said thermoelastic metal alloy rod in said first deformed-shape configuration through said proximate end into said internal lumen of said surgically introduced catheter such that an on-demand controlled extension and retraction of said metal rod through said internal lumen of said catheter is achieved;

controllably extending a portion of said thermoelastic metal alloy rod on-demand through said internal lumen to exit via said distal end of said surgically introduced and adjacently positioned catheter into the in-vivo temperature environment of the living body such that said exiting portion of said thermoelastic metal alloy transforms into said memory-shaped second configuration; and extending the remainder of said thermoelastic metal alloy rod on-demand through said internal lumen to exit via said distal end of said surgically introduced and adjacently positioned catheter into the in-vivo temperature environment of the living body such that said exiting memory-shaped second configuration of said metal alloy at least partially overlays the ruptured segment of the therapeutic appliance as an in-vivo repair.

2. An in-vivo method for repairing a ruptured segment of a retention wire in a pacemaker lead which has been previously surgically positioned within the body of a living human, said in-vivo repair method comprising the steps of:

providing at least one metal alloy rod of predetermined dimensions and comprised of a deformable thermoelastic shape-memory alloy, at least a portion of said thermoelastic metal rod being substantially in a first deformed-shape configuration at temperatures less than about 25°–35° C. while transforming into a memory-shaped second configuration at temperatures greater than about 25°–35° C.;

providing a controlling flexible catheter having at least one tubular wall of set axial length, at least one proximal end for entry, at least one distal end for egress, and at least one internal lumen of a volume sufficient to allow for on-demand controlled passage therethrough of said thermoelastic metal rod;

surgically introducing a portion of the axial length of said controlling flexible catheter into the body of the living human such that said distal end of said surgically introduced catheter becomes positioned adjacent to the ruptured segment of the retention wire of the pacemaker lead in-vivo;

maintaining at least a portion of said internal lumen of said surgically introduced catheter at a temperature less than about 25°–35° C.;

placing said thermoelastic metal alloy rod in said first deformed-shape configuration through said proximal end into said internal lumen of said surgically introduced catheter such that an on-demand controlled extension and retraction of said metal rod through said internal lumen of said catheter is achieved;

controllably extending a portion of said thermoelastic metal alloy rod on-demand through said internal lumen to exit via said distal end of said surgically introduced and adjacently positioned catheter into the in-vivo temperature environment of the living body such that said exiting portion of said thermoelastic metal alloy transforms into said memory-shaped second configuration; and extending the remainder of said thermoelastic metal alloy rod on-demand through said internal lumen to exit via said distal end of said surgically introduced and adjacently positioned catheter into the in-vivo temperature environment of the living body such that said exiting memory-shaped second configuration of said metal alloy at least partially overlays the ruptured segment of the retention wire in the pacemaker lead as an in-vivo repair.

3. The in-vivo method for repair as recited in claim 1 or 2 wherein said metal alloy rod is a single strand of wire.

4. The in-vivo method for repair as recited in claim 1 or 2 wherein said metal alloy rod comprises multiple strands of wire.

5. The in-vivo method for repair as recited in claim 1 or 2, wherein said metal alloy rod is a substantially planar ribbon.

6. The in-vivo method for repair as recited in claim 1 or 2 wherein said metal alloy rod is a substantially tubular filament.

7. The in-vivo method for repair as recited in claim 1 or 2 wherein said metal rod is a multi-faceted strip.

8. The in-vivo method for repair as recited in claim 1 or 2 wherein said controlling flexible catheter comprises a single internal lumen.

9. The in-vivo method for repair as recited in claim 1 or 2 wherein said controlling flexible catheter comprises multiple internal lumens.

10. The in-vivo method for repair as recited in claim 1 or 2 wherein said controlling flexible catheter comprises a single external tubular wall.

11. The in-vivo method for repair as recited in claim 1 or 2 wherein said controlling flexible catheter comprises multiple external tubular walls.

12. The in-vivo method for repair as recited in claim 1 or 2 wherein said controlling flexible catheter comprises a single proximal portal as the means for entry into said internal lumen volume.

13. The in-vivo method for repair as recited in claim 1 or 2 wherein said controlling flexible catheter comprises a plurality of proximal portals as means for entry into said internal lumen volume.

14. The in-vivo method for repair as recited in claim 1 or 2 wherein said controlling flexible catheter comprises a single distal portal as the means for egress from said internal lumen volume.

15. The in-vivo method for repair as recited in claim 1 or 2 wherein said controlling flexible catheter comprises a plurality of distal portals as means for egress from said internal lumen volume.

* * * * *